United States Patent [19]

McMullen et al.

[11] Patent Number: 5,569,828
[45] Date of Patent: Oct. 29, 1996

[54] MAIZE CHLOROTIC DWARF VIRUS AND RESISTANCE THERETO

[75] Inventors: Michael D. McMullen, Wooster, Ohio; Bradley A. Roth, Grimes; Rod Townsend, Des Moines, both of Iowa

[73] Assignees: Pioneer Hi-Bred International, Inc., Des Moines, Iowa; The United States of America as represented by the Department of Agriculture, Washington, D.C.

[21] Appl. No.: 38,768

[22] Filed: Mar. 24, 1993

[51] Int. Cl.$^6$ .................... A01M 1/02; A01M 4/00; A01M 5/00; C12N 5/04; C12N 7/00; C12N 15/33; C12N 15/34

[52] U.S. Cl. .................... 800/205; 800/250; 800/DIG. 9; 800/DIG. 52; 800/DIG. 56; 536/23.72; 435/69.1; 435/172.3; 435/240.4; 435/240.5; 435/252.3; 435/320.1; 47/58

[58] Field of Search .................... 424/405, 418; 435/69.1, 170, 172.1, 172.3, 252.3, 320.1, 240.1, 240.4, 240.5; 800/200, 205, 250, DIG. 56, DIG. 9, DIG. 52; 536/23.72, 27, 23.1; 47/58

[56] References Cited

PUBLICATIONS

Wilson, T. Michael A. (1993) "Strategies to protect crop plants against viruses: Pathogen–derived resistance blossoms", *Proc. Natl. Acad. Sci. USA*, 90:3134–3141.

Nelson et al. 1988. Bio/Technology. 6:403–409.

Abel et al. 1986. Science. 232: 738–743.

Ge et al. 1989. Phytopathology. 79(10):1195.

Forsberg et al. 1980. *In*Hybridization of Crop Plants. Fehr et al. eds. Ch. 4:65–81.

Abersold et al. 1987. Proc. Natl. Acad. Sci USA. 84:6970–6974.

Berger et al. 1989. J. Gen. Virol. 70:1845–1851.

Sambrook et al. 1989. Molecular Cloning. pp. 11.1–11.19, 11.45–11.61.

Gordon–Kamm et al. 1990. The Plant Cell. vol. 2: 603–618.

Potrykus. 1991. Annu. Rev. Plant Physiol. Plant Mol. Biol. 42:205–225.

*Primary Examiner*—David T. Fox
*Assistant Examiner*—Erich E. Veitenmeimer

[57] ABSTRACT

Methods and materials are provided to isolate the coat protein genes from maize chlorotic dwarf virus. One or more of these genes (MCDV-CP$_1$, MCDV-CP$_2$ or MCDV-CP$_3$) is then incorporated in an expression cassette designed for suitable expression in a plant cell system. The resulting transformation vector is then introduced into maize to provide cross-protection to MCDV or related viral infections.

20 Claims, 1 Drawing Sheet

5,569,828

MAIZE CHLOROTIC DWARF VIRUS AND RESISTANCE THERETO

TECHNICAL FIELD

This invention relates to providing plants with resistance to maize chlorotic dwarf virus (MCDV) and viruses to which MCDV infection or resistance provides cross-resistance, including maize dwarf mosaic virus strain A (MDMV-A).

BACKGROUND OF THE INVENTION

Virus-induced diseases in agronomically important crops have cost farmers a great loss of income due to reduced yields. Traditionally, virus diseases have been controlled by breeding for host plant resistance or by controlling insects that transmit diseases. Chemical means of protection are not generally possible for most viruses, and where possible are not generally practical. It has been known for many years that viral symptoms can be reduced in virus-infected plants by prior inoculation with a mild strain of the same virus, a phenomena known as cross-protection, as described by Sequeira, L., *Trends in Biotechnology*, 2, 25 (1984). Cross-protection is considered successful if the disease symptoms of the superinfecting (the more virulent) virus can be delayed or suppressed. There are several disadvantages to applying this type of cross-protection to the field situation:

1) application of the mild strain virus to entire fields is usually not practical,
2) the mild strain might undergo mutation to a more highly virulent strain,
3) the protecting strain might interact synergistically with a non-related virus causing a severe pathogenic infection,
4) a protecting virus in one crop may be a severe pathogen in another crop, and
5) a protective strain may cause a significant loss of yield in itself.

One proposed solution to these disadvantages has been to introduce a single viral gene into the host plant genome to cross-protect, rather than infect with an intact virus. This single gene cross-protection strategy has already been proven successful using the coat protein gene from tobacco mosaic virus (TMV-CP). As reported by Abel, P. P., et. al., *Science*, 232, 738 (1986), transgenic tobacco plants, expressing TMV mRNA and coat protein (CP), demonstrated delayed or suppressed symptom development upon infection with TMV. TMV-CP transgenic tomato plants have been described by Nelson, R. S., et. al., *Bio/Technology*, 6, 403 (1988), to show evidence of protection from TMV as well as three strains of tomato mosaic virus (ToMV). Other approaches using DNA clones of viruses to engineer resistance include positive interference, as described by Golemboski et al. *Proc. Natl. Acad. Sci. USA*, 87, 6311 (1990) and Carr and Zaitlin, *Mol. Pl. Microbe Inter.*, 4, 579 (1991); and antisense RNA, as described by Powell et al., *Proc. Natl. Acad. Sci. USA*, 86, 6949 (1989).

Numerous viruses exist for which resistance is desired. Maize chlorotic dwarf virus causes a somewhat variable mosaic or yellow streaking and occasional stunting in maize. Early infections can result in severe symptoms including premature death. The virus is spread by the blackfaced leafhopper (*Graminella nigrifons*). MCDV can overwinter in Johnsongrass (*Sorghum halepense*) and as a result has become a recurrent problem in areas where Johnsongrass is a common weed. Combined infections with maize dwarf mosaic virus can cause more severe symptoms although the syndrome is less well characterized than Corn Lethal Necrosis. Only limited success has been obtained to date in developing MCDV-resistant maize lines, due to the difficulties of selecting efficiently for resistance to an obligately insect transmitted virus, as well as a lack of usable sources of resistance in agronomically useful maize lines. Thus, there is a continuing need for genes, plant transformation vectors, and transformed plant materials providing resistances to pathogenic viruses such as MCDV.

Unfortunately, while certain plant viruses, such as tobacco mosaic virus, have coat protein genes that are found on subgenomic RNA and are therefore relatively easy to identify and clone for use in engineered cross-protection, maize chlorotic dwarf virus belongs to a completely separate group, the only other (tentatively assigned) member of which is the spherical virus of the rice tungro disease (RTSV). In addition, MCDV has a number of unusual biological properties which make identification of an appropriate gene difficult. For example, all attempts to mechanically transmit MCDV have been unsuccessful. As another example, MCDV appears to be a phloem-restricted virus. MCDV also has three coat proteins, and it was not known whether expression of one protein would be sufficient to confer immunity or whether all three would need to be expressed. Nor was it known which protein would be the appropriate one to express if only one could be expressed. Further, the genome of MCDV has an unusual genome organization to provide for the expression of multiple coat proteins.

BRIEF DESCRIPTION OF THE DRAWING FIGURES

DISCLOSURE OF THE INVENTION

Figure 1:
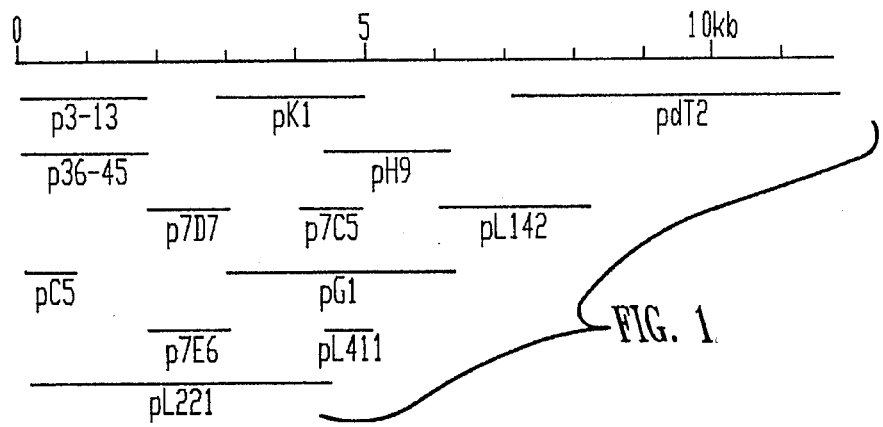
FIG. 1 is a schematic illustration of the manner in which the nucleic acid sequence of MCDV-type strain was obtained by sequencing overlapping cDNA clones.

In the present invention, methods and materials are provided to isolate any or all of the three coat protein genes from maize chlorotic dwarf virus (MCDV). One or more of these genes (MCDV-$CP_x$, where x is 1, 2, or 3) is then incorporated in an expression cassette designed for suitable expression in a plant cell system. The resulting transformation vector is then introduced into maize callus to provide cross-protection to MCDV-related viral infections. MCDV has a single, long RNA core having the sequence shown in SEQUENCE I.D. No. 4.

DESCRIPTION OF THE PREFERRED EMBODIMENTS

The present invention provides cDNA clones from the RNA genome of maize chlorotic dwarf virus which code substantially solely for the coat protein of the virus. These clones are incorporated into an expression cassette in which the cDNA clone is operably linked to plant or bacterial regulatory sequences which cause the expression of the cDNA clone in living plant or bacterial cells, respectively. It is important that the cloned gene have a start codon in the correct reading frame for the structural sequence. The resulting bacterial vectors can be readily inserted into bacteria for expression and characterization of the sequence. Accordingly, the present invention also provides bacterial cells containing as a foreign plasmid at least one copy of the foregoing bacterial expression cassette. In addition, the plant expression cassette preferably includes a strong constitutive promoter sequence at one end to cause the gene to be transcribed at a high level and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa, as disclosed in U.S. patent application Ser. No. 07/785,648, filed Oct. 31, 1991. Highly preferred plant expression cassettes will be designed to include one or more selectable marker genes, such as kanamycin resistance or herbicide tolerance genes. The plant expression vectors of this invention can be inserted, using any convenient technique, including electroporation (in protoplasts), microprojectile bombardment, and microinjection, into cells from monocotyledonous or dicotyledonous plants, in cell or tissue culture, to provide transformed plant cells containing as foreign DNA at least one copy of the DNA sequence of the plant expression cassette. Preferably, the monocotyledonous species will be selected from maize, sorghum, wheat and rice, and the dicotyledonous species will be selected from soybean, alfalfa, tobacco and tomato. Using known techniques, protoplasts can be regenerated and cell or tissue culture can be regenerated to form whole fertile plants which carry and express the desired cDNA clone for MCDV coat protein. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to maize chlorotic dwarf virus to plants of a MCDV susceptible taxon, comprising the steps of:
   a) culturing cells or tissues from at least one plant from the taxon,
   b) introducing into the cells of the cell culture or tissue culture at least one copy of an expression cassette comprising a cDNA clone from the RNA genome of MCDV which codes substantially solely for the coat protein of the virus, operably linked to plant regulatory sequences which cause the expression of the cDNA clone in the cells, and
   c) regenerating MCDV-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the coat protein gene and associated regulatory sequence via crossing and backcrossing. Such intermediate methods will comprise the further steps of
   a) sexually crossing the MCDV resistant plant with a plant from the MCDV susceptible-taxon;
   b) recovering reproductive material from the progeny of the cross; and
   c) growing resistant plants from the reproductive material. Where desirable or necessary, the characteristics of the susceptible taxon can be substantially preserved by expanding this method to include the further steps of repetitively:
      a) backcrossing the MCDV resistant progeny with MCDV susceptible plants from the susceptible taxon; and
      b) selecting for expression of MCDV resistance among the progeny of the backcross,
until the desired percentage of the characteristics of the susceptible taxon are present in the progeny along with the gene imparting MCDV resistance.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens* or *Agrobacterium rhizogenes*, which can then be used to transfer the vector into susceptible plant cells, primarily from dicotyledonous species. Thus, this invention provides a method for imparting MCDV resistance in Agrobacterium-susceptible dicotyledonous plants in which the expression cassette is introduced into the cells by infecting the cells with *Agrobacterium tumefaciens*, a plasmid of which has been modified to include the plant expression cassette of this invention. The following description further exemplifies the compositions of this invention and the methods of making and using them. However, it will be understood that other methods, known by those of ordinary skill in the art to be equivalent, can also be employed.

1. Isolation and cloning of MCDV cDNA

The type strain of MCDV was maintained in the maize inbred Oh28 by transmission with the leafhopper *G. nigrifrons* and viral particles were isolated as previously described (Hunt et al., *Phytopathology* 78, 449 (1988)). MCDV particles were suspended in NETS (10 mM Tris, pH 7.5; 100 mM NaCl; 1 mM Na$_2$EDTA; 0.5% SDS) and extracted with 1:1 chloroform:phenol to isolate MCDV RNA.

First and second strand cDNA synthesis were by the method of Gubler and Hoffman, *Gene* 25, 263 (1983) utilizing cDNA synthesis kits (Amersham, Arlington Heights, Ill.). For the initial cDNA libraries, double-stranded cDNA was treated with EcoRI methylase, ligated to GGAATTCC EcoRI linkers, digested with EcoRI and separated from linkers by column fractionation. The cDNA was ligated to EcoRI-cleaved _gt10 and EcORI-cleaved, phosphatased (CIP) _gt11 phage arms. After packaging, the _gt10 phage were plated on bacterial strain NM514 and screened for MCDV-specific inserts by filter plaque hybridization (Benton and Davis, *Science* 196, 180 (1977)), using $^{32}$P-labeled cDNA's random-primed from the MCDV genomic RNA. MCDV-positive phage were purified and the cDNA inserts subcloned into pUC119 (Vieira and Messing, *Meth. Enzymol.* 153, 3 (1987)) for further analysis. Hybridization positive clones from the initial gt10 library included: p3–13, p36–45, pH9, pK1, pG1, pC5 (FIG. 1). After packaging, the _gt11 phage were plated on bacterial strain Y1090⁻ and screened with antisera to either intact MCDV virions or isolated, individual MCDV capsid proteins (Maroon, MS Thesis, Ohio State University (1989)) as described by Mierendorf, et al. *Meth. Enzymol.* 152,458 (1987). Positive phage clones were identified with antisera specific to either cp1 or cp2, and cDNA inserts from these phage were subcloned into pUC119. The anti-cp1-specific cDNA clone, p7C5, and the anti-cp2-specific cDNA clones, p7E6 and p7D7, (FIG. 1) were chosen for study. Analysis of initial cDNAs revealed that a number of clones terminated at identical EcoRI sites which were shown to be present in the viral sequence. This result indicated that the methylation of the initial cDNAs was incomplete. To obtain cDNAs to the rest of MCDV and to overlap the initial clones, two additional cDNA libraries were prepared, one primed with oligo-dT(12–18) and one random-primed. Double-stranded cDNA prepared as above was ligated to a 20/24 nt. blunt end/EcoRI adaptor (Amersham), and adaptor cDNAs were kinased and ligated to EcoRI-cleaved/phosphatased pUC119. Plasmid clone pdT2 (FIG. 1) was derived from the dT-primed library and plasmids pL142, pL221, and pL411 (FIG. 1) were derived from the random-primed library.

2. Sequencing of MCDV cDNA

Single-stranded DNA templates for sequencing were derived by superinfection with M13K07 of bacterial strain MV1190 containing the pUC119 based cDNAs (FIG. 1), cloned in both orientations, as described by McMullen et al., *Nuc. Acids Res.*, 14, 4953 (1986) and Vieira and Messing, *Meth. Enzymol.* 153, 3 (1987). Ordered deletions from the full-length single-stranded templates were prepared by the method of Dale et al., *Plasmid* 13, 31 (1985). Dideoxynudeotide sequencing reactions with the Klenow fragment of Pol. I or Sequenase (U.S. Biochemicals, Cleveland, Ohio) were performed using $^{35}$S-dATP. Greater than 99% of the total sequence was obtained from both strands and the majority was read from three or more templates. The 5' sequence not contained on cDNA was obtained by direct RNA sequencing, using the sequencing primer 5'-GGTCTACTCACGGCACGCCA-3' (SEQUENCE I.D. NO. 3) with an RNA sequencing kit (Boehringer Mannheim, Indianapolis, Ind.) as recommended except that tailing of reaction products with dTTP by terminal deoxynucleotidyl transferase using the method of DeBorde et al., *Anal. Biochem.* 157,275 (1986) was added to improve resolution of final bases.

To obtain the amino-terminal protein sequence of MCDV capsid proteins, MCDV particles were disrupted in Laemmli loading buffer and the individual capsid protein separated on a 12.5%–4% Laemmli slab gel (Laemmli, *Nature* 227, 680 (1970)). The proteins were electrotransfered to Immobilon-P membrane (Millipore, Bedford, Mass.) using a 10 mM CAPS, pH 11.0; 10% MeOH transfer buffer, stained with Coomassie Blue R-250 for visualization and excised. Automated amino-terminal protein sequencing was performed by the Iowa State University Biochemistry Instrumentation Center (Ames, Iowa).

DNA and protein sequence analysis was performed using the IntelliGenetics (Mountain View, Calif.) molecular biology software on a Digital VAX 8250 located at the USDA-ARS-ASRR (Agricultural Systems Research Resource) Beltsville, Md.

The nucleic acid sequence of MCDV-type strain was obtained by sequencing overlapping cDNA clones (FIG. 1) that covered all but 13 nucleotides at the 5' terminus of MCDV. The 5' end sequence was obtained by direct RNA sequencing. Despite repeated attempts and the use of terminal transferase in the manner of DeBorde et al., *Anal. Biochem.*, 157, 275 (1986) the first nucleotide could not be definitely determined. In part for this reason, the expressions "coding substantially for" and "coding substantially solely for" are used herein, and with regard to the use of the word "substantially" refer to sequences which code for no more than a few (five or less) amino acids greater or lesser on either end of the desired protein or proteins, or which have an equivalent number of nucleotide bases more or less than the native sequence.

The genomic RNA of MCDV-type (SEQUENCE I.D. NO. 4) was determined to be 11785 nucleotides long, exclusive of the poly-A tail at the 3' terminus. This sequence permits the construction of a DNA molecule which codes for the entire maize chlorotic dwarf virus, or any portion or functional unit thereof which is useful in conferring resistance to the virus when expressed in plant cells. Such resistance can readily be evaluated using routine testing methods such as those disclosed herein. Computer analysis of the sequence indicated a long open reading frame from nucleotide 456 to nucleotide 10826. The translation of this open reading frame would result in a protein of 3457 and no acids with a derived molecular weight of 388,890 daltons. The open reading frame begins with two AUG triplets, neither of which is in a particularly favorable context for initiation of translation when compared with the analyses of translation start sequences by Lutcke et al., *EMBO J.* 6, 43 (1987); and Kosak, *J. Cell Biol.* 108, 229 (1989) by the scanning model. In addition, there are 13 AUG triplets preceding the double AUG that starts the open reading frame. A long untranslated 3' leader containing multiple AUG triplets before the beginning of a very long reading frame is similar to the animal picornaviruses as described by Stanway, *J. Gen. Virol.* 71, 2483 (1990). Internal initiation at the AUG for the long open reading frame has been demonstrated to occur for a number of the animal picornaviruses as seen in Pelletier and Sonenberg, *Nature,* 334, 320 (1988) and Jang et al., *J. Virol.,* 63, 1651 (1989). The mechanism for initiation of translation for MCDV has not been characterized.

The derived amino acid sequence of MCDV-type was compared to the Protein Identification Resource, Version 32 and the University of Geneva, Version 22, protein data banks for sequence similarity using the IFIND (IntelliGenetics) program based on the algorithm of Wilber and Lipman, *Proc. Natl. Acad. Sci. USA,* 80, 726 (1983). The highest similarity score was with the comovirus, cowpea mosaic virus (CPMV) as reported by Lomonossoff and Shanks, *EMBO J.,* 2, 2253 (1983) and the second highest score was with the nepovirus, grapevine fanleaf virus (GFLV) as reported by Ritzenthaler et al., *J. Gen. Virol.,* 72, 2357 (1991). For both viruses the region of similarity preceded and included the first conserved motif of RNA-dependent RNA polymerases as defined by Poch et al. *EMBO J.,* 8, 3867 (1989). The IFIND program identified weaker similarity with additional nepoviruses and some of the animal picornaviruses. The conservation of protein sequence and gene order for the plant comoviruses, nepoviruses and potyviruses, and the animal picornaviruses is well documented by, inter alia, Agros et al., *Nuc. Acids Res.,* 12, 7251 (1984); Goldbach, *Ann. Rev. Phytopath.,* 24, 289 (1986); and Domier et al., *Virology,* 158, 20 (1987) and has led to the proposal of the picornavirus-like "supergroup". Two additional conserved protein regions involved in genome replication for picorna-like viruses are the NTP binding/helicase region, as described by Agros et al., above, and Gorbalenya et al., *Nuc. Acids Res.,* 17, 4713 (1989) and the C-terminal region, cysteine active site of the 3C-like proteases, as also described by Agros et al., above, and by Grief et al., *J. Gen. Virol.,* 69, 1517 (1988).

The electrophoresis of MCDV virions on denaturing protein gels reveals three structural proteins, designated cp1, cp2 and cp3 with molecular weights of 32.5 kd, 27 kd, and 24.5 kd; respectively. Antiserum specific to cp1 was used to screen a _gt11 library to isolate the clone p7C5, and antiserum specific to cp2 was used to identify the cDNAs p7E6 and p7D7 (FIG. 1). This result indicated that an antigenic region of cp1 was located between 4063–4903 and an antigenic region of cp2 was located between 1815–2941.

Automated amino-terminal sequencing was performed on each of the MCDV capsid proteins. The amino-terminus of cp2 was apparently blocked as no sequence was obtained. The 15 amino acids at the $NH_2$-terminus of cp3 were determined to be LQVASLTDIGELSSV, as shown in SEQUENCE I.D. NO. 2 and SEQUENCE I.D. NO. 6. This sequence is an exact match to the derived protein sequence encoded by nucleotides 3144–3188. Likewise, the 15 amino acids at the $NH_2$-terminus of cp1, VSLGRSFENGVLIGS, as shown in SEQUENCE I.D. NO. 5 and SEQUENCE I.D. NO. 7, are an exact match to the derived protein sequence encoded by nucleotides 3750–3794. Both proteins must be derived by proteolytic cleavage of the large polyprotein. The Gln/Leu cleavage at the $NH_2$-terminus of cp3 and Gln/Val cleavage at the $NH_2$-terminus of cp1 are dipeptide cleavage sites that may be used by animal picornavirus 3C proteases, according to Krausslich and Wimmer, *Ann. Rev. Biochem.*, 57, 754 (1988), which could indicate that the 3C-similar region of the MCDV may function in capsid protein processing. Assuming that cp3 begins with the Leu at the Gln/Leu cleavage and ends with the Gln at the Gln/Val cleavage for cp1, cp3 would have a derived MW of 21,933, a little less than the 24.5 kd MW determined by SDS gel electrophoresis. Although protein sequence was not obtained for cp2, the position of clones p7E6 and p7D7, and the finding that protein fusions expressed from the pEX vector for the PstI fragments 2076–2619 and 2613–3149 reacted positively with cp2-specific antiserum (McMullen, unpublished), is consistent with cp2 preceding cp3 in the polyprotein similar to the order of vp2-vp3-vp1 for the animal picornaviruses. However, it is still not known if the coding region for cp2 immediately precedes cp3.

Figure 2:
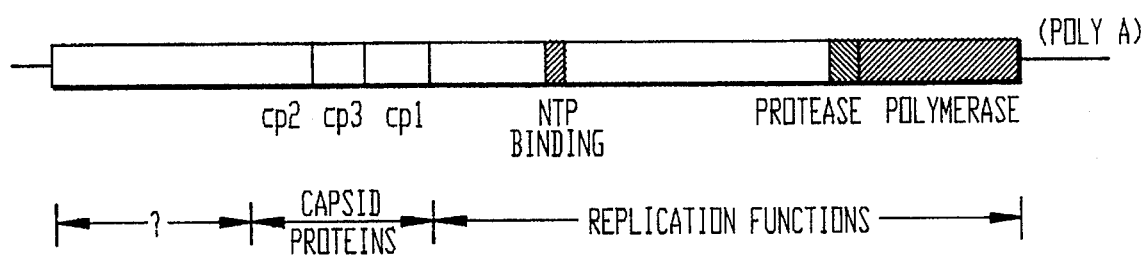
FIG. 2 is an a schematic illustration of the unusual organization of the MCDV genome.

The overall genome structure of MCDV-type strain is shown in FIG. 2. MCDV genome organization resembled that of the animal picornaviruses, a single large polyprotein in which the capsid proteins are encoded 5' of the proteins presumed to be involved in genome replication. Depending on the exact location of cp2, the MCDV genome can encode up to 78 kd of protein 5' of the capsid proteins for which there are no corresponding animal picornavirus protein. This region may encode plant virus specific functions such as cell-to-cell movement or helper protein for insect transmission. Because MCDV is a phloem restricted virus, there is no evidence for a virus-encoded cell-to-cell movement protein. However, there is evidence for the presence of an insect transmission helper component in MCDV-infected plants according to Hunt et al., *Phytopathology*, 78, 449 (1988). The presence of plant-virus-specific proteins at the $NH^2$-terminus of the polyprotein would allow addition of these proteins without disruption of the cp proteins-replication functions genome structure typical of picornaviruses.

3. Design of the plasmid vector.

The gene MCDV coat protein 3 was placed under control of tandem cauliflower mosaic virus 35S promoters isolated from the 1841 strain of the virus, and a polyadenylation signal sequence obtained from the potato proteinase inhibitor II (Pin II) gene that exhibits enhancer-like activity. The chimeric gene also included a 79 bp sequence Ω' from the 5' leader region of tobacco mosaic virus (TMV) that functions as a translational enhancer; and a *Zea mays* alcohol dehydrogenase 1, intron 1 fragment (ADH) spanning nucleotides 119–672, trimmed to 557 bp with Bal 31 nuclease, which has been shown to function as an enhancer of gene expression in monocots. The plasmids were grown in *E. coli* and purified by the known polyethylene glycol precipitation method of Sambrook et al., *Molecular Cloning*, 1, 40 (1989). Purity was confirmed by electrophoretic analysis of the DNA fragments obtained after digestion with restriction endonucleases. The plasmid was designated pPHI1406 and the sequence is shown in SEQUENCE I.D. No. 1.

4. Preparation of the recipient organism.

Separately, an embryogenic cell suspension line 54-68-5 was established from immature embryos obtained from a cross between a line derived from the public inbred corn line B73 and a WX 1–9 translocation stock of public inbred corn line W23.

5. Transformation

Suspension cells from (4) were bombarded with 1 µl aliquots of a 30 µl mixture containing 10 µg of purified plasmid DNA (5 µg of the MCDV plasmid pPHI1406 (SEQUENCE I.D. No. 1), and 5 µg of the same plasmid in which the BAR (Basta resistance) gene was substituted for the MCDV cp3 gene) precipitated onto 1 µm tungsten particles as described by numerous articles including Klein, T. M., et al., 1988 (May) *Bio/Technology* 6:559–563; Klein, T. M., et al., 1988 (June) *Proc. Natl. Acad. Sci.* U.S.A. 85:4305–4309; T. M. Klein, et al., "Stable Genetic Transformation of Intact Applicant Nicotiana Cells by the Particle Bombardment Process", *Proc. Natl. Acad. Sci. USA*, Vol. 85, November 1988, pp. 8502–8505; D. T. Tomes, et al., "Transgenic Tobacco Plants and their Progeny Derived by Microprojectile Bombardment of Tobacco Leaves", *Plant Molecular Biology*, Vol. 14, No. 2, February, 1990, pp. 261–268, Kluwer Academic Publishers, BE; and M. C. Ross, et al., "Transient and Stable Transgenic Cells and Calli of Tobacco and Maize Following Microprojectile Bombardment", *J. Cell. Biochem.*, Suppl. 13D, 27th Mar.–April 1989, P. 268, Abstract No. M. 149, Alan R. Liss, Inc. New York, U.S.; and plated onto selective medium containing 5 ppb phosphinothricin (Basta™).

Following a prolonged period of selection and callus growth, regeneration was initiated by placing callus on a Murashige & Skoog medium modified by addition of 0.5 mg/l 2,4-D and 5 ppb Basta. Embryogenic callus was selected and transferred to medium lacking 2,4-D and kept in a lighted growth room. Germinated plantlets were placed in culture tubes and finally planted out into soil in pots in the greenhouse.

More than 150 $R_0$ (recombinant) plants were obtained, representing twenty independent transformation events. Transformation was confirmed by PCR amplification of a DNA fragment spanning part of the MCDV coat protein gene and the CaMV promoter. Genomic DNA samples, in which a fragment of the expected size was successfully amplified were presumed to be transformed. These plants were pollinated with pollen from non-transgenic B73 plants and the resulting $R_1$ seed was planted in a field trial under USDA supervision. The resulting plants exhibited a virus resistant phenotype, i.e., they survived and set seed under virus infection conditions in which non-transgenic plants died prematurely, as seen in the following table:

| Field Test Results | | |
| --- | --- | --- |
| | Transgenic | Control |
| Number of Plants | 379 | 32 |
| Number of Harvestable Ears | 52 | 0 |
| % Harvested vs. Total | 13.7% | 0% |

The screening was performed in a manner to insure maximum infection levels and severity. Thus, the level of resistance seen in this extreme test corresponds to effective, usable virus tolerance when the transformants of this invention are used trader normal farming conditions.

The MCDV resistance is a simply inherited, dominant trait and can, if desired, be introduced into other maize varieties by simple crossing or backcrossing. In addition to providing resistance to MCDV, this invention is also capable of conferring resistance to viruses to which plants obtain cross-resistance through infection by MCDV. In the field test described above, resistance to maize dwarf mosaic virus strain A (MDMV-A) was also observed. Accordingly, this invention provides resistance to that virus as well.

What is claimed is:

1. A DNA clone coding substantially solely for a coat protein of maize chlorotic dwarf virus.

2. An expression cassette comprising a DNA clone according to claim 1, operably linked to plant regulatory sequences which cause the expression of the DNA clone in plant cells.

3. An expression cassette comprising a DNA clone according to claim 1, operably linked to bacterial expression regulatory sequences which cause the expression of the DNA clone in bacterial cells.

4. Bacterial cells containing as a foreign plasmid at least one copy of an expression cassette according to claim 3.

5. Transformed plant cells containing as foreign DNA at least one copy of the DNA sequence of an expression cassette according to claim 2.

6. Transformed cells according to claim 5, further characterized in being cells of a monocotyledonous species.

7. Transformed cells according to claim 6, further characterized in being maize, sorghum, wheat or rice cells.

8. Transformed cells according to claim 5, further characterized in being cells of a dicotyledonous species.

9. Transformed cells according to claim 8, further characterized in being soybean, alfalfa, tobacco or tomato cells.

10. A maize cell or tissue culture comprising cells according to claim 7.

11. A transformed maize plant, the cells of which contain as foreign DNA at least one copy of the DNA sequence of an expression cassette according to claim 2.

12. A method of imparting resistance to maize chlorotic dwarf virus and maize dwarf mosaic virus-A to plants of a MCDV or MDMV-A susceptible taxon, comprising the steps of:

a) culturing cells or tissues from at least one plant from the taxon, b) introducing into the cells of the cell culture or tissue culture at least one copy of an expression cassette comprising a DNA clone from the RNA genome of MCDV which codes substantially solely for the coat protein of the virus, operably linked to plant regulatory sequences which cause the expression of the DNA clone in the cells, and c) regenerating MCDV-resistant whole plants from the cell culture or tissue culture.

13. A method according to claim 12 which comprises the further step of sexually or clonally reproducing the whole plants in such manner that at least one copy of the sequence provided by the expression cassette is present in the cells of progeny of the reproduction.

14. A method according to claim 12 in which the expression cassette is introduced into the cells by electroporation.

15. A method according to claim 12 in which the expression cassette is introduced into the cells by microparticle bombardment.

16. A method according to claim 12 in which the expression cassette is introduced into the cells by microinjection.

17. A method according to claim 13 for providing MCDV and MDMV-A resistance in *Agrobacterium tumefaciens*-susceptible dicotyledonous plants in which the expression cassette is introduced into the cells by infecting the cells with *Agrobacterium tumefaciens*, a plasmid of which has been modified to include the expression cassette.

18. A method of imparting resistance to maize chlorotic dwarf virus and maize dwarf mosaic virus strain A to plants of a MCDV or MDMV-A susceptible taxon, comprising the steps of:

a) selecting a fertile, MCDV resistant plant prepared by the method of claim 12 from a sexually compatible taxon;

b) sexually crossing the MCDV resistant plant with a plant from the MCDV susceptible taxon;

c) recovering reproductive material from the progeny of the cross; and d) growing resistant plants from the reproductive material.

19. A method according to claim 18 which comprises the further steps of repetitively:

a) backcrossing the MCDV resistant progeny with MCDV susceptible plants from the susceptible taxon; and b) selecting for expression of MCDV resistance among the progeny of the backcross, until the desired percentage of the characteristics of the susceptible taxon are present in the progeny along with MCDV resistance.

20. A DNA molecule coding for maize chlorotic dwarf virus or a portion thereof which is capable of conferring resistance to maize chlorotic dwarf virus when expressed in a plant cell.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 5033 base pairs
        ( B ) TYPE: nucleotide
        ( C ) STRANDEDNESS: double
        ( D ) TOPOLOGY: linear ( i i ) MOLECULE TYPE: synthetic DNA
        ( A ) DESCRIPTION: transformation plasmid pPHI1406

( i i i ) HYPOTHETICAL: No ( x i ) SEQUENCE DESCRIPTION: SEQ ID NO: 1:

```
TCGCGCGTTT   CGGTGATGAC   GGTGAAAACC   TCTGACACAT   GCAGCTCCCG                50
GAGACGGTCA   CAGCTTGTCT   GTAAGCGGAT   GCCGGGAGCA   GACAAGCCCG               100
TCAGGGCGCG   TCAGCGGGTG   TTGGCGGGTG   TCGGGCTGG    CTTAACTATG               150
CGGCATCAGA   GCAGATTGTA   CTGAGAGTGC   ACCATATGCG   GTGTGAAATA               200
CCGCACAGAT   GCGTAAGGAG   AAAATACCGC   ATCAGGCGCC   ATTCGCCATT               250
CAGGCTGCGC   AACTGTTGGG   AAGGGCGATC   GGTGCGGGCC   TCTTCGCTAT               300
TACGCCAGCT   GGCGAAAGGG   GGATGTGCTG   CAAGGCGATT   AAGTTGGGTA               350
ACGCCAGGGT   TTTCCCAGTC   ACGACGTTGT   AAAACGACGG   CCAGTGCCAA               400
GCTCAGATCT   GAGCTTCTAG   AAATCCGTCA   ACATGGTGGA   GCACGACACT               450
CTCGTCTACT   CCAAGAATAT   CAAAGATACA   GTCTCAGAAG   ACCAAAGGGC               500
TATTGAGACT   TTTCAACAAA   GGGTAATATC   GGGAAACCTC   CTCGGATTCC               550
ATTGCCCAGC   TATCTGTCAC   TTCATCAAAA   GGACAGTAGA   AAAGGAAGGT               600
GGCACCTACA   AATGCCATCA   TTGCGATAAA   GGAAAGGCTA   TCGTTCAAGA               650
TGCCTCTGCC   GACAGTGGTC   CCAAAGATGG   ACCCCCACCC   ACGAGGAGCA               700
TCGTGGAAAA   AGAAGACGTT   CCAACCACGT   CTTCAAAGCA   AGTGGATTGA               750
TGTGATGCTC   TAGAAATCCG   TCAACATGGT   GGAGCACGAC   ACTCTCGTCT               800
ACTCCAAGAA   TATCAAAGAT   ACAGTCTCAG   AAGACCAAAG   GGCTATTGAG               850
ACTTTTCAAC   AAAGGGTAAT   ATCGGGAAAC   CTCCTCGGAT   TCCATTGCCC               900
AGCTATCTGT   CACTTCATCA   AAAGGACAGT   AGAAAAGGAA   GGTGGCACCT               950
ACAAATGCCA   TCATTGCGAT   AAAGGAAAGG   CTATCGTTCA   AGATGCCTCT              1000
GCCGACAGTG   GTCCCAAAGA   TGGACCCCCA   CCCACGAGGA   GCATCGTGGA              1050
AAAGAAGAC   GTTCCAACCA   CGTCTTCAAA   GCAAGTGGAT   TGATGTGATA              1100
TCTCCACTGA   CGTAAGGGAT   GACGCACAAT   CCCACTATCC   TTCGCAAGAC              1150
CCTTCCTCTA   TATAAGGAAG   TTCATTTCAT   TTGGAGAGGA   CGAGCTGCAG              1200
CTTATTTTTA   CAACAATTAC   CAACAACAAC   AAACAACAAA   CAACATTACA              1250
```

| | | | | |
|---|---|---|---|---|
| ATTACTATTT | ACAATTACAG | TCGACGGATC | AAGTGCAAAG | GTCCGCCTTG | 1300
| TTTCTCCTCT | GTCTCTTGAT | CTGACTAATC | TTGGTTTATG | ATTCGTTGAG | 1350
| TAATTTTGGG | GAAAGCTTCG | TCCACAGTTT | TTTTTTCGAT | GAACAGTGCC | 1400
| GCAGTGGCGC | TGATCTTGTA | TGCTATCCTG | CAATCGTGG | GAACTTATGT | 1450
| CTTTTATATC | CTTCACTACC | ATGAAAAGAC | TAGTAATCTT | TCTCGATGTA | 1500
| ACATCGTCCA | GCACTGCTAT | TACCGTGTGG | TCCATCCGAC | AGTCTGGCTG | 1550
| AACACATCAT | ACGATATTGA | GCAAAGATCG | ATCTATCTTC | CCTGTTCTTT | 1600
| AATGAAAGAC | GTCATTTTCA | TCAGTATGAT | CTAAGAATGT | TGCAACTTGC | 1650
| AAGGAGGCGT | TTCTTTCTTT | GAATTTAACT | AACTCGTTGA | GTGGCCCTGT | 1700
| TTCTCGGACG | TAAGGCCTTT | GCTGCTCCAC | ACATGTCCAT | TCGAATTTTA | 1750
| CCGTGTTTAG | CAAGGGCGAA | AAGTTTGCAT | CTTGATGATT | TAGCTTGACT | 1800
| ATGCGATTGC | TTTCCTGGAC | CCGTGCAGCT | GCGGACGGAT | CCACCATGGC | 1850
| ACTGCAGGTG | GCATCTCTTA | CAGACATAGG | AGAATTGAGC | AGTGTGGTTG | 1900
| CTACTGGTTC | TTGGTCTACT | ACCTCGGCTA | CTAATTTGAT | GGAATTAAAC | 1950
| ATTCATCCCA | CCTCCTGTGC | TATTCAGAAC | GGATTGATAA | CACAGACACC | 2000
| ATTGAGTGTT | TTAGCTCATG | CTTTTGCAAG | GTGGAGAGGA | TCGTTGAAAA | 2050
| TTTCCATCAT | TTTCGGAGCG | AGTTTGTTTA | CCCGAGGACG | AATCTTAGCC | 2100
| GCTGCTGTGC | CCGTTGCTAA | GCGCAAAGGT | ACCATGAGCC | TTGACGAGAT | 2150
| TAGTGGGTAT | CATAATGTTT | GCTGCTTATT | GAATGGTCAG | CAAACTACAT | 2200
| TTGAATTGGA | AATCCCATAT | TATTCTGTGG | GCCAAGATTC | TTTCGTGTAC | 2250
| CGTGATGCTC | TTTTTGATAT | CTCTGCGCAC | GATGGGAATT | TTATGATTAC | 2300
| TCGCTTGCAT | CTCGTGATAC | TGGATAAATT | GGTAATGAGC | GCTAATGCGA | 2350
| GCAACAGCAT | AAATTTTCC | GTGACTCTTG | GACCAGGTTC | TGATTTGGAA | 2400
| TTGAAATATC | TTGCAGGAGT | ACATGGGCAG | CGCATAGTCC | GCGAGTTGAA | 2450
| GATGCAGTGA | TCAACCTAGA | CTTGTCCATC | TTCTGGATTG | GCCAACTTAA | 2500
| TTAATGTATG | AAATAAAAGG | ATGCACACAT | AGTGACATGC | TAATCACTAT | 2550
| AATGTGGGCA | TCAAAGTTGT | GTGTTATGTG | TAATTACTAG | TTATCTGAAT | 2600
| AAAAGAGAAA | GAGATCATCC | ATATTTCTTA | TCCTAAATGA | ATGTCACGTG | 2650
| TCTTTATAAT | TCTTTGATGA | ACCAGATGCA | TTTCATTAAC | CAAATCCATA | 2700
| TACATATAAA | TATTAATCAT | ATATAATTAA | TATCAATTGG | GTTAGCAAAA | 2750
| CAAATCTAGT | CTAGGTGTGT | TTTGCGAATT | GCGGCCGCGA | TCTGGGGAAT | 2800
| TCGTAATCAT | GGTCATAGCT | GTTTCCTGTG | TGAAATTGTT | ATCCGCTCAC | 2850
| AATTCCACAC | AACATACGAG | CCGGAAGCAT | AAAGTGTAAA | GCCTGGGGTG | 2900
| CCTAATGAGT | GAGCTAACTC | ACATTAATTG | CGTTGCGCTC | ACTGCCCGCT | 2950
| TTCCAGTCGG | GAAACCTGTC | GTGCCAGCTG | CATTAATGAA | TCGGCCAACG | 3000
| CGCGGGGAGA | GGCGGTTTGC | GTATTGGGCG | CTCTTCCGCT | TCCTCGCTCA | 3050
| CTGACTCGCT | GCGCTCGGTC | GTTCGGCTGC | GGCGAGCGGT | ATCAGCTCAC | 3100
| TCAAAGGCGG | TAATACGGTT | ATCCACAGAA | TCAGGGGATA | ACGCAGGAAA | 3150
| GAACATGTGA | GCAAAAGGCC | AGCAAAAGGC | CAGGAACCGT | AAAAAGGCCG | 3200
| CGTTGCTGGC | GTTTTTCCAT | AGGCTCCGCC | CCCCTGACGA | GCATCACAAA | 3250

-continued

```
AATCGACGCT CAAGTCAGAG GTGGCGAAAC CCGACAGGAC TATAAAGATA        3300
CCAGGCGTTT CCCCCTGGAA GCTCCCTCGT GCGCTCTCCT GTTCCGACCC        3350
TGCCGCTTAC CGGATACCTG TCCGCCTTTC TCCCTTCGGG AAGCGTGGCG        3400
CTTTCTCATA GCTCACGCTG TAGGTATCTC AGTTCGGTGT AGGTCGTTCG        3450
CTCCAAGCTG GGCTGTGTGC ACGAACCCCC CGTTCAGCCC GACCGCTGCG        3500
CCTTATCCGG TAACTATCGT CTTGAGTCCA ACCCGGTAAG ACACGACTTA        3550
TCGCCACTGG CAGCAGCCAC TGGTAACAGG ATTAGCAGAG CGAGGTATGT        3600
AGGCGGTGCT ACAGAGTTCT TGAAGTGGTG GCCTAACTAC GGCTACACTA        3650
GAAGGACAGT ATTTGGTATC TGCGCTCTGC TGAAGCCAGT TACCTTCGGA        3700
AAAAGAGTTG GTAGCTCTTG ATCCGGCAAA CAAACCACCG CTGGTAGCGG        3750
TGGTTTTTTT GTTTGCAAGC AGCAGATTAC GCGCAGAAAA AAGGATCTC         3800
AAGAAGATCC TTTGATCTTT TCTACGGGGT CTGACGCTCA GTGGAACGAA        3850
AACTCACGTT AAGGGATTTT GGTCATGAGA TTATCAAAAA GGATCTTCAC        3900
CTAGATCCTT TTAAATTAAA AATGAAGTTT TAAATCAATC TAAAGTATAT        3950
ATGAGTAAAC TTGGTCTGAC AGTTACCAAT GCTTAATCAG TGAGGCACCT        4000
ATCTCAGCGA TCTGTCTATT TCGTTCATCC ATAGTTGCCT GACTCCCCGT        4050
CGTGTAGATA ACTACGATAC GGGAGGGCTT ACCATCTGGC CCCAGTGCTG        4100
CAATGATACC GCGAGACCCA CGCTCACCGG CTCCAGATTT ATCAGCAATA        4150
AACCAGCCAG CCGGAAGGGC CGAGCGCAGA AGTGGTCCTG CAACTTTATC        4200
CGCCTCCATC CAGTCTATTA ATTGTTGCCG GGAAGCTAGA GTAAGTAGTT        4250
CGCCAGTTAA TAGTTTGCGC AACGTTGTTG CCATTGCTAC AGGCATCGTG        4300
GTGTCACGCT CGTCGTTTGG TATGGCTTCA TTCAGCTCCG GTTCCCAACG        4350
ATCAAGGCGA GTTACATGAT CCCCCATGTT GTGCAAAAAA GCGGTTAGCT        4400
CCTTCGGTCC TCCGATCGTT GTCAGAAGTA AGTTGGCCGC AGTGTTATCA        4450
CTCATGGTTA TGGCAGCACT GCATAATTCT CTTACTGTCA TGCCATCCGT        4500
AAGATGCTTT TCTGTGACTG GTGAGTACTC AACCAAGTCA TTCTGAGAAT        4550
AGTGTATGCG GCGACCGAGT TGCTCTTGCC CGGCGTCAAT ACGGGATAAT        4600
ACCGCGCCAC ATAGCAGAAC TTTAAAAGTG CTCATCATTG GAAAACGTTC        4650
TTCGGGGCGA AAACTCTCAA GGATCTTACC GCTGTTGAGA TCCAGTTCGA        4700
TGTAACCCAC TCGTGCACCC AACTGATCTT CAGCATCTTT TACTTTCACC        4750
AGCGTTTCTG GGTGAGCAAA AACAGGAAGG CAAAATGCCG CAAAAAAGGG        4800
AATAAGGGCG ACACGGAAAT GTTGAATACT CATACTCTTC CTTTTTCAAT        4850
ATTATTGAAG CATTTATCAG GGTTATTGTC TCATGAGCGG ATACATATTT        4900
GAATGTATTT AGAAAAATAA ACAAATAGGG GTTCCGCGCA CATTTCCCCG        4950
AAAAGTGCCA CCTGACGTCT AAGAAACCAT TATTATCATG ACATTAACCT        5000
ATAAAAATAG GCGTATCACG AGGCCCTTTC GTC                          5033
```

( 2 ) INFORMATION FOR SEQ ID NO: 2:

( i ) SEQUENCE CHARACTERISTICS:
        ( A ) LENGTH: 45 bases
        ( B ) TYPE: nucleotide
        ( C ) STRANDEDNESS: single
        ( D ) TOPOLOGY: linear (ii) MOLECULE TYPE: viral RNA
    (A) DESCRIPTION: RNA codons for first 15 amino acids at 5'
        end of MCDV coat protein 3 (CP3)

(iii) HYPOTHETICAL: No (xi) SEQUENCE DESCRIPTION: SEQ ID NO: 2:

| CUG | CAG | GUG | GCA | UCU | CUU | ACA | GAC | AUA | GGA | GAA | UUG | AGC | AGU | GUG | 45 |
| Leu | Gln | Val | Ala | Ser | Leu | Thr | Asp | Ile | Gly | Asp | Leu | Ser | Ser | Val | |
|     |     |     |     | 5   |     |     |     |     | 10  |     |     |     |     | 15  | |

(2) INFORMATION FOR SEQ ID NO: 3:

(i) SEQUENCE CHARACTERISTICS:
       (A) LENGTH: 20 bases
       (B) TYPE: nucleotide
       (C) STRANDEDNESS: single
       (D) TOPOLOGY: linear (ii) MOLECULE TYPE: synthetic DNA
       (A) DESCRIPTION: sequencing primer (iii) HYPOTHETICAL: No (xi) SEQUENCE DESCRIPTION: SEQ ID NO: 3:

GGTCTACTCA CGGCACGCCA                                                                 20

(2) INFORMATION FOR SEQ ID NO: 4:

(i) SEQUENCE CHARACTERISTICS:
       (A) LENGTH: 11785 bases
       (B) TYPE: nucleotide
       (C) STRANDEDNESS: single
       (D) TOPOLOGY: linear (ii) MOLECULE TYPE: viral RNA (iii) HYPOTHETICAL: No (xi) SEQUENCE DESCRIPTION: SEQ ID NO: 4:

NUGAAAAGGA GGGUAUAGAG AUACCCUUCA UAUAUUCUGC GGAUGGCGUG                    50

CCGUGAGUAG ACCUCGCGAC GUUUCCCAGA GGAAAAUGGA AAUGGUCCAU                    100

GUAACACCAG AUAUUUAUCU GGUUGAGGAA CAUGGUUUAG UGGUAGAGAU                    150

AAACUCAACU UUGUGUUGGA CCCCGAUGCU GUGAAAAGUA AAUAAAGACA                    200

AGGCCACUUA GCGAAGGAUA UUCGAAGUAG UGAUGAAAGG AAGUGCAAUA                    250

AGUCAUGCCG UAAGUCGCAA UGCGCUAUAA GUCAUGCCGU AAGCCGCGUC                    300

GCCUGGAUUU GCUAUUAGAA UGUCCCUAGC CGGUGAUAAC CUUGAGUCCC                    350

CGUCAUAGGA CUACUUUUGU UUGCUUAGUA AUACAUUGGG ACCACCCGCA                    400

UGGAGCUCUG AGCCUACCAU ACAUAGUACA UUUUCCGAGG GAUUGUCUUU                    450

| UGAUA |     | AUG | AUG | CAG | ACA | AAC | AAC | AAC | CAA | AAU | CCC |     | 485 |
|       |     | Met | Met | Gln | Thr | Asn | Asn | Asn | Gln | Asn | Pro |     |     |
|       |     |     |     |     |     | 5   |     |     |     |     | 10  |     |     |

| ACU | CAA | GGA | AGC | AUU | CCU | GAG | AAC | UCC | UCA | CAA | GAU | CGC | AAC | UUA | 530 |
| Thr | Gln | Gly | Ser | Ile | Pro | Glu | Asn | Ser | Ser | Gln | Asp | Arg | Asn | Leu | |
|     |     |     |     | 15  |     |     |     |     | 20  |     |     |     |     | 25  | |

| GGA | GUG | CCC | GCU | GGA | UAU | UCU | UUA | AGC | GUU | GAG | GAC | CCC | UUC | GGG | 575 |
| Gly | Val | Pro | Ala | Gly | Tyr | Ser | Leu | Ser | Val | Glu | Asp | Pro | Phe | Gly | |
|     |     |     |     | 30  |     |     |     |     | 35  |     |     |     |     | 40  | |

| AAC | CGG | UCU | GAC | UUU | CAU | AUC | CCA | GUG | CAC | CAA | AUC | AUU | CGG | GAA | 620 |
| Asn | Arg | Ser | Asp | Phe | His | Ile | Pro | Val | His | Gln | Ile | Ile | Arg | Glu | |
|     |     |     |     | 45  |     |     |     |     | 50  |     |     |     |     | 55  | |

-continued

| | | | | | | | | | | | | | | | |
|---|---|---|---|---|---|---|---|---|---|---|---|---|---|---|---|
| GAG | AUU | GAU | CGU | CCA | AAU | UGG | GUU | CCU | AUA | UGU | UCA | AAC | GAU | UUU | 665 |
| Glu | Ile | Asp | Arg | Pro 60 | Asn | Trp | Val | Pro | Ile 65 | Cys | Ser | Asn | Asp | Phe 70 | |
| CAU | CUU | AAC | AGU | GAG | GAU | UAU | UGU | GAG | GAG | UGC | GAA | UCU | GAA | CGG | 710 |
| His | Leu | Asn | Ser | Glu 75 | Asp | Tyr | Cys | Glu | Glu 80 | Cys | Asp | Ser | Asp | Arg 85 | |
| AUC | AAA | AAU | UUC | GAA | AUA | UUC | AGA | UCA | CAG | AAU | UUG | AUU | GAC | CAA | 755 |
| Ile | Lys | Asn | Phe | Asp 90 | Ile | Phe | Arg | Ser | Gln 95 | Asn | Leu | Ile | Asp | Gln 100 | |
| CAC | CUA | AAU | CUC | UGU | ACU | GAU | UCA | AAG | GAU | UGU | GAU | CAU | UUU | UCU | 800 |
| His | Leu | Asn | Leu | Cys 105 | Thr | Asp | Ser | Lys | Asp 110 | Cys | Asp | His | Phe | Ser 115 | |
| UGU | UUU | UCC | ACG | AGU | ACA | AGU | UGC | AGA | UUU | UGC | CCU | UUU | UGC | UUA | 845 |
| Cys | Phe | Ser | Thr | Ser 120 | Thr | Ser | Cys | Arg | Phe 125 | Cys | Pro | Phe | Cys | Leu 130 | |
| UUC | AUU | UUU | AAU | UUG | GAU | AAA | UUU | UAC | AAA | CAA | AAU | CUA | UAU | UUG | 890 |
| Phe | Ile | Phe | Asn | Leu 135 | Asp | Lys | Phe | Tyr | Lys 140 | Gln | Asn | Leu | Tyr | Leu 145 | |
| AUU | AGU | CGU | CAG | GCU | CUA | GCU | AGA | UUG | UUC | CAC | GGA | AGC | GCC | GAA | 935 |
| Ile | Ser | Arg | Gln | Ala 150 | Leu | Ala | Arg | Leu | Phe 155 | His | Gly | Ser | Ala | Asp 160 | |
| GAG | UUA | CUC | AGU | AGA | GCG | AUU | UUC | UUU | ACG | UAU | AAU | AUU | UGU | AUU | 980 |
| Glu | Leu | Leu | Ser | Arg 165 | Ala | Ile | Phe | Phe | Thr 170 | Tyr | Asn | Ile | Cys | Ile 175 | |
| GAU | GCA | GAG | GUG | GUU | GCU | AAU | AAU | AGG | AUU | GGC | UGU | GAA | UAU | GUU | 1025 |
| Asp | Ala | Glu | Val | Val 180 | Ala | Asn | Asn | Arg | Ile 185 | Gly | Cys | Asp | Tyr | Val 190 | |
| AAG | UUG | UUU | CAU | CCA | GAC | CUU | AGG | CCU | AGU | AUU | ACG | UCU | CCC | CCU | 1070 |
| Lys | Leu | Phe | His | Pro 195 | Asp | Leu | Arg | Pro | Ser 200 | Ile | Thr | Ser | Pro | Pro 205 | |
| UAU | GCU | AGU | GAU | UGG | GUU | AUG | UGU | GAU | AAU | GCU | AAA | CAU | CUU | UUU | 1115 |
| Tyr | Ala | Ser | Asp | Trp 210 | Val | Met | Cys | Asp | Asn 215 | Ala | Lys | His | Leu | Phe 220 | |
| GAG | UGU | CUU | GGC | CUU | GGU | GAC | ACG | ACC | AGA | GGA | CAC | CUA | UAU | GGA | 1160 |
| Glu | Cys | Leu | Gly | Leu 225 | Gly | Asp | Thr | Thr | Arg 230 | Gly | His | Leu | Tyr | Gly 235 | |
| CUU | AUU | AGC | GAG | AAU | GCA | UAU | UGG | AAC | GCC | ACG | UGC | UCA | AAA | UGC | 1205 |
| Leu | Ile | Ser | Glu | Asn 240 | Ala | Tyr | Trp | Asn | Ala 245 | Thr | Cys | Ser | Lys | Cys 250 | |
| GGA | GCC | UGU | UGU | CAG | GGA | GCA | AAU | GCC | CGU | ACG | GCG | AUA | CCG | AUA | 1250 |
| Gly | Ala | Cys | Cys | Gln 255 | Gly | Ala | Asn | Ala | Arg 260 | Thr | Ala | Ile | Pro | Ile 265 | |
| GUG | AUG | GCG | UUG | CAG | UAC | UGC | AGG | GUG | GAU | GUG | UAU | UAU | AGU | GAG | 1295 |
| Val | Met | Ala | Leu | Gln 270 | Tyr | Cys | Arg | Val | Asp 275 | Val | Tyr | Tyr | Ser | Glu 280 | |
| UAC | UAU | UUA | UAC | CAC | AUC | UAC | GCU | CCG | GAA | GAG | AGA | AUG | AAG | AUU | 1340 |
| Tyr | Tyr | Leu | Tyr | His 285 | Ile | Tyr | Ala | Pro | Asp 290 | Glu | Arg | Met | Lys | Ile 295 | |
| GAU | CAA | CAG | ACA | GCA | CAC | UUG | CUA | CAC | AGU | AUA | AUC | CGA | GGA | GCA | 1385 |
| Asp | Gln | Gln | Thr | Ala 300 | His | Leu | Leu | His | Ser 305 | Ile | Ile | Arg | Gly | Ala 310 | |
| CCA | GCA | GUG | GAU | UGC | UCU | GAG | UUA | UCU | CAG | GAG | CCA | AUU | CAC | AGG | 1430 |
| Pro | Ala | Val | Asp | Cys 315 | Ser | Glu | Leu | Ser | Gln 320 | Glu | Pro | Ile | His | Arg 325 | |
| AUG | GUA | AUG | GAU | AGC | UCA | AAG | UUA | GUG | GCA | CUG | GAU | UCG | ACA | AUC | 1475 |
| Met | Val | Met | Asp | Ser 330 | Ser | Lys | Leu | Val | Ala 335 | Leu | Asp | Ser | Thr | Ile 340 | |
| AGG | CAU | CCU | AAG | AGC | CAA | GGA | AGU | UUG | CUC | GAU | UCA | GAA | UGC | GAU | 1520 |
| Arg | His | Pro | Lys | Ser 345 | Gln | Gly | Ser | Leu | Leu 350 | Asp | Ser | Asp | Cys | Asp 355 | |

| | | | | | | | | | | | | | | |
|---|---|---|---|---|---|---|---|---|---|---|---|---|---|---|
| CAU | GAG | UUU | AUU | CUA | AGA | ACG | UCC | CAU | GGU | AUC | AAA | AUA | CCG | AUG | 1565 |
| His | Glu | Phe | Ile | Leu 360 | Arg | Thr | Ser | His 365 | Gly | Ile | Lys | Ile | Pro | Met 370 | |
| AGU | AAG | UCU | UUA | UUU | AUA | UCA | UUU | CUU | ACC | AUG | GGA | GCU | UAU | CAU | 1610 |
| Ser | Lys | Ser | Leu | Phe 375 | Ile | Ser | Phe | Leu | Thr 400 | Met | Gly | Ala | Tyr | His 405 | |
| GGG | UAU | GCU | CAU | GAU | GAU | CAG | CAG | GAG | CAA | AAU | GCG | AUA | AUA | UCU | 1655 |
| Gly | Tyr | Ala | His | Asp 410 | Asp | Gln | Gln | Glu | Gln 415 | Asn | Ala | Ile | Ile | Ser 420 | |
| UUU | GGU | GGG | AUG | CCC | GGA | GUC | AAU | UUG | GCU | UGU | AAC | AAA | AAU | UUC | 1700 |
| Phe | Gly | Gly | Met | Pro 425 | Gly | Val | Asn | Leu | Ala 430 | Cys | Asn | Lys | Asn | Phe 435 | |
| CUG | AGA | AUG | CAU | AAG | UUG | UUU | UAU | UCU | GGA | AGU | UUU | AGG | CGC | AGA | 1745 |
| Leu | Arg | Met | His | Lys 440 | Leu | Phe | Tyr | Ser | Gly 445 | Ser | Phe | Arg | Arg | Arg 450 | |
| CCC | CUG | UUU | AUG | AGC | CAA | AUU | CCC | UCU | ACG | AAU | GCC | ACC | GCU | CAG | 1790 |
| Pro | Leu | Phe | Met | Ser 455 | Gln | Ile | Pro | Ser | Thr 460 | Asn | Ala | Thr | Ala | Gln 465 | |
| UCC | GGU | UUU | AAU | GAU | GAA | GAA | UUC | GAA | AGA | UUG | AUG | GCU | GAA | GAG | 1835 |
| Ser | Gly | Phe | Asn | Asp 470 | Asp | Asp | Phe | Asp | Arg 475 | Leu | Met | Ala | Asp | Glu 480 | |
| GGU | GUG | CAU | GUC | AAA | GUC | GAG | CGU | CCA | AUA | GCA | GAG | AGG | UUU | GAU | 1880 |
| Gly | Val | His | Val | Lys 485 | Val | Glu | Arg | Pro | Ile 490 | Ala | Glu | Arg | Phe | Asp 500 | |
| UAU | GAG | GAC | GUU | AUU | GAU | AUU | UAC | GAU | GAG | ACC | GAC | CAC | GAC | AGG | 1925 |
| Tyr | Glu | Asp | Val | Ile 505 | Asp | Ile | Tyr | Asp | Glu 510 | Thr | Asp | His | Asp | Arg 515 | |
| ACA | CGA | GCU | CUA | GGC | CUU | GGC | CAA | GUA | UUC | GGA | GGU | UUG | CUC | AAA | 1970 |
| Thr | Arg | Ala | Leu | Gly 520 | Leu | Gly | Gln | Val | Phe 525 | Gly | Gly | Leu | Leu | Lys 530 | |
| GGA | AUU | UCU | CAU | UGU | GUA | GAU | AGC | CUA | CAU | AAG | GUA | UUU | GAU | UUC | 2015 |
| Gly | Ile | Ser | His | Cys 535 | Val | Asp | Ser | Leu | His 540 | Lys | Val | Phe | Asp | Phe 545 | |
| CCU | CUG | GAC | CUG | GCC | AUA | GAA | GCA | GCU | CAG | AAA | ACU | GGU | GAU | UGG | 2060 |
| Pro | Leu | Asp | Leu | Ala 550 | Ile | Asp | Ala | Ala | Gln 555 | Lys | Thr | Gly | Asp | Trp 560 | |
| CUU | GAA | GGA | AAU | AAA | GCU | GCA | GUA | GAU | GAA | ACU | AAA | AUU | UGU | GUG | 2105 |
| Leu | Asp | Gly | Asn | Lys 565 | Ala | Ala | Val | Asp | Asp 670 | Thr | Lys | Ile | Cys | Val 675 | |
| GGC | UGU | CCC | GAG | AUU | CAA | AAA | GAU | AUG | AUC | AGU | UUC | CAG | AAU | GAA | 2150 |
| Gly | Cys | Pro | Glu | Ile 580 | Gln | Lys | Asp | Met | Ile 585 | Ser | Phe | Gln | Asn | Asp 590 | |
| ACA | AAA | GAA | GCU | UUU | GAA | UUA | AUA | CGA | UCA | AGU | AUA | AAG | AAG | CUU | 2195 |
| Thr | Lys | Asp | Ala | Phe 595 | Asp | Leu | Ile | Arg | Ser 600 | Ser | Ile | Lys | Lys | Leu 605 | |
| UCC | GAG | GGC | AUU | GAC | AAA | AUC | ACG | AAG | AUG | AAU | GCU | ACG | AAC | UUU | 2240 |
| Ser | Glu | Gly | Ile | Asp 610 | Lys | Ile | Thr | Lys | Met 615 | Asn | Ala | Thr | Asn | Phe 620 | |
| GAA | CGA | AUC | CUA | GAC | GGG | AUU | AAA | CCA | AUC | GAG | AGC | AGG | UUG | ACA | 2285 |
| Asp | Arg | Ile | Leu | Asp 625 | Gly | Ile | Lys | Pro | Ile 630 | Glu | Ser | Arg | Leu | Thr 635 | |
| GAA | CUU | GAG | AAC | AAG | GCA | CCC | GCU | UCA | GAC | AGC | AAA | GCC | AUG | GAA | 2330 |
| Asp | Leu | Glu | Asn | Lys 640 | Ala | Pro | Ala | Ser | Asp 645 | Ser | Lys | Ala | Met | Asp 650 | |
| GCU | CUG | GUC | CAG | GCC | GUG | AAA | GAC | UUG | AAA | AUC | AUG | AAA | GAG | GCG | 2375 |
| Ala | Leu | Val | Gln | Ala 655 | Val | Lys | Asp | Leu | Lys 660 | Ile | Met | Lys | Glu | Ala 665 | |
| AUG | CUC | GAU | CUA | AAU | CGA | AGA | CUG | AGC | AAG | CUG | GAA | GGA | AAG | AAA | 2420 |
| Met | Leu | Asp | Leu | Asn 670 | Arg | Arg | Leu | Ser | Lys 675 | Leu | Asp | Gly | Lys | Lys 680 | |

```
AGU GAU GGC CAG ACU ACU GAA GGG ACA GCG GGA GAG CAA CAA CCG         2465
Ser Asp Gly Gln Thr Thr Asp Gly Thr Ala Gly Glu Gln Gln Pro
            685             690                     695

AUC CCU AAG ACU CCA ACU CGA GUG AAG GCA AGA CCA GUU GUG AAG         2510
Ile Pro Lys Thr Pro Thr Arg Val Lys Ala Arg Pro Val Val Lys
            700             705                     710

CAA UCA GGA ACG AUA AUG GUA AAC GAA GAG AGC ACA GAA ACU UUC         2555
Gln Ser Gly Thr Ile Met Val Asn Asp Glu Ser Thr Asp Thr Phe
            715             720                     725

AGG GAU AAU GAG AGU CGA GUG ACU GAC CCU AAC AGG AGC GAU AUG         2600
Arg Asp Asn Glu Ser Arg Val Thr Asp Pro Asn Arg Ser Asp Met
            730             735                     740

UUU GCU GCU GUU ACU GCA GAA UAC UUA GUU AAA UCG UUU ACA UGG         2645
Phe Ala Ala Val Thr Ala Asp Tyr Leu Val Lys Ser Phe Thr Trp
            745             750                     755

AAA GUU UCU GAU GGA CAA GAU AAA GUU UUG GCU GAC CUU GAU UUA         2690
Lys Val Ser Asp Gly Gln Asp Lys Val Leu Ala Asp Leu Asp Leu
            760             765                     770

CCU CAA GAC UUA UGG AAA UCC AAU UCC CGA UUG AGU GAU AUC AUG         2735
Pro Gln Asp Leu Trp Lys Ser Asn Ser Arg Leu Ser Asp Ile Met
            775             780                     785

GGG UAU UUC CAA UAU UAU GAU GCA ACC GGA AUC ACU UUU CGC AUA         2780
Gly Tyr Phe Gln Tyr Tyr Asp Ala Thr Gly Ile Thr Phe Arg Ile
            790             795                     800

ACG ACA ACA UGU GUU CCU AUG CAC GGU GGU ACU UUA UGU GCU GCU         2825
Thr Thr Thr Cys Val Pro Met His Gly Gly Thr Leu Cys Ala Ala
            805             810                     815

UGG GAU GCU AAU GGU UGC GCU ACA CGA CAA GGU AUA GCC ACA ACG         2870
Trp Asp Ala Asn Gly Cys Ala Thr Arg Gln Gly Ile Ala Thr Thr
            820             825                     830

GUU CAG CUG ACU GGU UUG CCC AAA ACA UUU AUU GAA GCU CAC AGC         2915
Val Gln Leu Thr Gly Leu Pro Lys Thr Phe Ile Asp Ala His Ser
            835             840                     845

UCA UCA GAA ACG AUA AUC GUG GUA AAG AAU UCC AAU AUA CAA UCC         2960
Ser Ser Asp Thr Ile Ile Val Val Lys Asn Ser Asn Ile Gln Ser
            850             855                     860

GCG AUU UGU CUA AGU GGA AGU GAG CAC UCG UUU GGG AGA AUG GGA         3005
Ala Ile Cys Leu Ser Gly Ser Glu His Ser Phe Gly Arg Met Gly
            865             870                     875

AUC CUG AAG AUC UGU UGC UUG AAU ACG UUG AAU GCG CCA AAG GAA         3050
Ile Leu Lys Ile Cys Cys Leu Asn Thr Leu Asn Ala Pro Lys Asp
            880             885                     890

GCU ACA CAG CAA GUG GCU GUG AAC GUC UGG AUU AAG UUU GAC GGA         3095
Ala Thr Gln Gln Val Ala Val Asn Val Trp Ile Lys Phe Asp Gly
            895             900                     905

GUU AAA UUU CAC GUU UAU UCU UUA AGG AAA AAU CCA GUC GUU UCG         3140
Val Lys Phe His Val Tyr Ser Leu Arg Lys Asn Pro Val Val Ser
            910             915                     920

CAA CUG CAG GUG GCA UCU CUU ACA GAC AUA GGA GAA UUG AGC AGU         3185
Gln Leu Gln Val Ala Ser Leu Thr Asp Ile Gly Asp Leu Ser Ser
            925             930                     935

GUG GUU GCU ACU GGU UCU UGG UCU ACU ACC UCG GCU ACU AAU UUG         3230
Val Val Ala Thr Gly Ser Trp Ser Thr Thr Ser Ala Thr Asn Leu
            940             945                     950

AUG GAA UUA AAC AUU CAU CCC ACC UCC UGU GCU AUU CAG AAC GGA         3275
Met Asp Leu Asn Ile His Pro Thr Ser Cys Ala Ile Gln Asn Gly
            955             960                     965

UUG AUA ACA CAG ACA CCA UUG AGU GUU UUA GCU CAU GCU UUU GCA         3320
Leu Ile Thr Gln Thr Pro Leu Ser Val Leu Ala His Ala Phe Ala
            970             975                     980
```

| | | | | | | | | | | | | | | | |
|---|---|---|---|---|---|---|---|---|---|---|---|---|---|---|---|
| AGG | UGG | AGA | GGA | UCG | UUG | AAA | AUU | UCC | AUC | AUU | UUC | GGA | GCG | AGU | 3365 |
| Arg | Trp | Arg | Gly | Ser 985 | Leu | Lys | Ile | Ser 990 | Ile | Ile | Phe | Gly | Ala | Ser 995 | |
| UUG | UUU | ACC | CGA | GGA | CGA | AUC | UUA | GCC | GCU | GCU | GUG | CCC | GUU | GCU | 3410 |
| Leu | Phe | Thr | Arg | Gly 1000 | Arg | Ile | Leu | Ala 1005 | Ala | Ala | Val | Pro | Val | Ala 1010 | |
| AAG | CGC | AAA | GGU | ACC | AUG | AGC | CUU | GAC | GAG | AUU | AGU | GGG | UAU | CAU | 3455 |
| Lys | Arg | Lys | Gly | Thr 1015 | Met | Ser | Leu | Asp 1020 | Glu | Ile | Ser | Gly | Tyr | His 1025 | |
| AAU | GUU | UGC | UGC | UUA | UUG | AAU | GGU | CAG | CAA | ACU | ACA | UUU | GAA | UUG | 3500 |
| Asn | Val | Cys | Cys | Leu 1030 | Leu | Asn | Gly | Gln 1035 | Gln | Thr | Thr | Phe | Asp | Leu 1040 | |
| GAA | AUC | CCA | UAU | UAU | UCU | GUG | GGC | CAA | GAU | UCU | UUC | GUG | UAC | CGU | 3545 |
| Asp | Ile | Pro | Tyr | Tyr 1045 | Ser | Val | Gly | Gln 1050 | Asp | Ser | Phe | Val | Tyr | Arg 1055 | |
| GAU | GCU | CUU | UUU | GAU | AUC | UCU | GCG | CAC | GAU | GGG | AAU | UUU | AUG | AUU | 3590 |
| Asp | Ala | Leu | Phe | Asp 1060 | Ile | Ser | Ala | His 1065 | Asp | Gly | Asn | Phe | Met | Ile 1070 | |
| ACU | CGC | UUG | CAU | CUC | GUG | AUA | CUG | GAU | AAA | UUG | GUA | AUG | AGC | GCU | 3635 |
| Thr | Arg | Leu | His | Leu 1075 | Val | Ile | Leu | Asp 1080 | Lys | Leu | Val | Met | Ser | Ala 1085 | |
| AAU | GCG | AGC | AAC | AGC | AUA | AAU | UUU | UCC | GUG | ACU | CUU | GGA | CCA | GGU | 3680 |
| Asn | Ala | Ser | Asn | Ser 1090 | Ile | Asn | Phe | Ser 1095 | Val | Thr | Leu | Gly | Pro | Gly 1100 | |
| UCU | GAU | UUG | GAA | UUG | AAA | UAU | CUU | GCA | GGA | GUA | CAU | GGG | CAG | CGC | 3725 |
| Ser | Asp | Leu | Asp | Leu 1105 | Lys | Tyr | Leu | Ala 1110 | Gly | Val | His | Gly | Gln | Arg 1115 | |
| AUA | GUC | CGC | GAG | UUG | AAG | AUG | CAG | GUU | UCA | UUG | GGU | CGG | UCA | UUU | 3770 |
| Ile | Val | Arg | Glu | Leu 1120 | Lys | Met | Gln | Val 1125 | Ser | Leu | Gly | Arg | Ser | Phe 1130 | |
| GAG | AAU | GGA | GUG | CUU | AUU | GGU | AGU | GGC | UUC | GAC | GAC | UUG | CUA | CAA | 3815 |
| Glu | Asn | Gly | Val | Leu 1135 | Ile | Gly | Ser | Gly 1140 | Phe | Asp | Asp | Leu | Leu | Gln 1145 | |
| AGA | UGG | AGU | CAU | UUG | GUG | UCC | AUG | CCU | UUU | AAU | GCA | AAA | GGA | GAC | 3860 |
| Arg | Trp | Ser | His | Leu 1150 | Val | Ser | Met | Pro 1155 | Phe | Asn | Ala | Lys | Gly | Asp 1160 | |
| AGC | GAU | GAG | AUC | CAA | GUC | UUU | GGC | UAU | AUC | AUG | ACU | GUU | GCC | CCG | 3905 |
| Ser | Asp | Glu | Ile | Gln 1165 | Val | Phe | Gly | Tyr 1170 | Ile | Met | Thr | Val | Ala | Pro 1175 | |
| GCG | UAU | CGU | UCC | CUU | CCA | GUC | CAC | UGC | ACG | CUG | CUA | AGU | UGG | UUU | 3950 |
| Ala | Tyr | Arg | Ser | Leu 1180 | Pro | Val | His | Cys 1185 | Thr | Leu | Leu | Ser | Trp | Phe 1190 | |
| UCA | CAA | UUA | UUC | GUG | CAG | UGG | AAA | GGU | GGU | AUA | AAG | UAU | AGA | CUA | 3995 |
| Ser | Gln | Leu | Phe | Val 1195 | Gln | Trp | Lys | Gly 1200 | Gly | Ile | Lys | Tyr | Arg | Leu 1205 | |
| CAC | AUU | GAU | UCA | GAA | GAG | CGC | AGA | UGG | GGU | GGA | UUC | AUC | AAA | GUU | 4040 |
| His | Ile | Asp | Ser | Asp 1210 | Glu | Arg | Arg | Trp 1215 | Gly | Gly | Phe | Ile | Lys | Val 1220 | |
| UGG | CAU | GAC | CCA | AAU | GGC | UCU | UUG | GAU | GAA | GGG | AAA | GAA | UUU | GCU | 4085 |
| Trp | His | Asp | Pro | Asn 1225 | Gly | Ser | Leu | Asp 1230 | Glu | Gly | Lys | Asp | Phe | Ala 1235 | |
| AAA | GCG | GAU | AUU | CUA | UCG | CCA | CCA | GCC | GGA | GCU | AUG | GUU | CGU | UAU | 4130 |
| Lys | Ala | Asp | Ile | Leu 1240 | Ser | Pro | Pro | Ala 1245 | Gly | Ala | Met | Val | Arg | Tyr 1250 | |
| UGG | AAC | UAU | UUA | AAU | GGA | GAC | UUG | GAG | UUU | ACA | GUA | CCA | UUU | UGU | 4175 |
| Trp | Asn | Tyr | Leu | Asn 1255 | Gly | Asp | Leu | Glu 1260 | Phe | Thr | Val | Pro | Phe | Cys 1265 | |
| GCU | AGA | ACC | AGU | ACG | CUG | UUC | AUA | CCA | AAA | GCU | AUG | AUU | GCC | ACC | 4220 |
| Ala | Arg | Thr | Ser | Thr 1270 | Leu | Phe | Ile | Pro 1275 | Lys | Ala | Met | Ile | Ala | Thr 1280 | |

| | | |
|---|---|---|
| GAU UCA AAG UCA UGG AUU CUG AAC UAC AAC GGU ACA UUG AAU UUC<br>Asp Ser Lys Ser Trp Ile Leu Asn Tyr Asn Gly Thr Leu Asn Phe<br>    1285              1290              1295 | | 4265 |
| GCG UAC CAA GGA GUA GAU GAC UUC ACA AUU ACA GUG GAA ACA AGU<br>Ala Tyr Gln Gly Val Asp Asp Phe Thr Ile Thr Val Asp Thr Ser<br>    1300              1305              1310 | | 4310 |
| GCA GCC GAC GAC UUU GAA UUU CAC GUU CGA ACA GUU GCA CCC CGC<br>Ala Ala Asp Asp Phe Glu Phe His Val Arg Thr Val Ala Pro Arg<br>    1315              1320              1325 | | 4355 |
| GCU GGA AAG GUC AAC GAA GCU UUU GCC AAA UUG GAG UAC GCU UCU<br>Ala Gly Lys Val Asn Asp Ala Phe Ala Lys Leu Glu Tyr Ala Ser<br>    1330              1335              1340 | | 4400 |
| GAU UUA AAG GAU AUC AAA GAA UCU CUG ACA UCU UCC ACU CGU UUG<br>Asp Leu Lys Asp Ile Lys Asp Ser Leu Thr Ser Ser Thr Arg Leu<br>    1345              1350              1355 | | 4445 |
| AAA GGG CCU CAU UAU AAA ACG AAA AUU ACC UCA AUA GAG CCA AAU<br>Lys Gly Pro His Tyr Lys Thr Lys Ile Thr Ser Ile Glu Pro Asn<br>    1360              1365              1370 | | 4490 |
| AAA AUU GAU GAA AAU GAG UCC UCA CGU GGU AAA GAU AAC AAG UCA<br>Lys Ile Asp Asp Asn Glu Ser Ser Arg Gly Lys Asp Asn Lys Ser<br>    1375              1380              1385 | | 4535 |
| AAU UCG AAA UUU GAG GAC UUA CUC AAU GCA ACA GCU CAG AUG GAU<br>Asn Ser Lys Phe Glu Asp Leu Leu Asn Ala Thr Ala Gln Met Asp<br>    1390              1395              1400 | | 4580 |
| UUU GAU CGA GCC ACA GCG AAC GUU GGG UGU GUG CCA UUC UCC AUU<br>Phe Asp Arg Ala Thr Ala Asn Val Gly Cys Val Pro Phe Ser Ile<br>    1405              1410              1415 | | 4625 |
| GCA AAG ACA GCA AAG GUG CUU UCG GAA CGC GAG ACG UGU AAG AAG<br>Ala Lys Thr Ala Lys Val Leu Ser Asp Arg Glu Thr Cys Lys Lys<br>    1420              1425              1430 | | 4670 |
| AUG GCA GAU GUG UUA GAU UUC ACA CAC UCA UGU UUG AAC UUA GAC<br>Met Ala Asp Val Leu Asp Phe Thr His Ser Cys Leu Asn Leu Asp<br>    1435              1440              1445 | | 4715 |
| AGU CAA CCU GCG GCG GCA AGA UUA GCA GCG GCC AUU UCU CAA AUA<br>Ser Gln Pro Ala Ala Ala Arg Leu Ala Ala Ala Ile Ser Gln Ile<br>    1500              1505              1510 | | 4760 |
| GCA CCU AUU AUG GAG AGC AUC GGU AGA ACC ACU CAA AGC GUA GAG<br>Ala Pro Ile Met Glu Ser Ile Gly Arg Thr Thr Gln Ser Val Glu<br>    1515              1520              1525 | | 4805 |
| GAA AAA UUG GCU UCU GUG GAU ACA UUU AGG GAC AAA AUC AUG GCU<br>Asp Lys Leu Ala Ser Val Asp Thr Phe Arg Asp Lys Ile Met Ala<br>    1530              1535              1540 | | 4850 |
| CUA AUU UCA AAC GUG CUU GGG GAU ACU CUA CCU GGA CUG GCC AUU<br>Leu Ile Ser Asn Val Leu Gly Asp Thr Leu Pro Gly Leu Ala Ile<br>    1545              1550              1555 | | 4895 |
| GCU GAC UUC AAA AAA GGA AAA UAU GUG UGG GCC UCG UUC CUG ACA<br>Ala Asp Phe Lys Lys Gly Lys Tyr Val Trp Ala Ser Phe Leu Thr<br>    1600              1605              1610 | | 4940 |
| AUG AUA GCC GCU UGC GUA GUA GCU UGG GCU GCC ACU AGC AAG AAA<br>Met Ile Ala Ala Cys Val Val Ala Trp Ala Ala Thr Ser Lys Lys<br>    1615              1620              1625 | | 4985 |
| AGC UUC UUG AAA AGA UUU GCA GUG GUA GCU AUG AUA AUU UGG AGC<br>Ser Phe Leu Lys Arg Phe Ala Val Val Ala Met Ile Ile Trp Ser<br>    1630              1635              1640 | | 5030 |
| CCA UUU CUC GCA AGU AAA AUA UGG GCG CUU GGU ACA UGG AUU AGG<br>Pro Phe Leu Ala Ser Lys Ile Trp Ala Leu Gly Thr Trp Ile Arg<br>    1645              1650              1655 | | 5075 |
| AAG AGC UGG AGU AAG CUU UGG CCU AAG UCA GAC UCA UGC CGA CAA<br>Lys Ser Trp Ser Lys Leu Trp Pro Lys Ser Asp Ser Cys Arg Gln<br>    1660              1665              1670 | | 5120 |

| | | | | | | | | | | | | | | |
|---|---|---|---|---|---|---|---|---|---|---|---|---|---|---|
| CAC | UCU | UUG | GCA | GGC | CUG | UGU | GAA | AGU | GUG | UUC | ACA | UCA | UUC | AAG | 5165 |
| His | Ser | Leu | Ala | Gly 1675 | Leu | Cys | Asp | Ser | Val 1680 | Phe | Thr | Ser | Phe | Lys 1685 | |
| GAU | UUC | CCU | GAC | UGG | UUU | AAA | UCA | GGA | GGA | AUC | ACG | AUU | GUG | ACG | 5210 |
| Asp | Phe | Pro | Asp | Trp 1690 | Phe | Lys | Ser | Gly | Gly 1695 | Ile | Thr | Ile | Val | Thr 1700 | |
| CAA | GUU | UGC | ACA | GUA | UUA | CUG | ACG | AUA | GUG | AGU | CUG | AUU | ACA | CUU | 5255 |
| Gln | Val | Cys | Thr | Val 1705 | Leu | Leu | Thr | Ile | Val 1710 | Ser | Leu | Ile | Thr | Leu 1715 | |
| GGA | ACU | AUA | CCA | AGC | ACG | AAA | CAA | AAU | GCU | ACG | UUC | GCA | GAC | AAA | 5300 |
| Gly | Thr | Ile | Pro | Ser 1720 | Thr | Lys | Gln | Asn | Ala 1725 | Thr | Phe | Ala | Asp | Lys 1730 | |
| UUU | AAA | GAA | UUU | GGU | AAC | AUG | AGC | AGA | GCU | ACA | ACG | UCA | AUA | GCU | 5345 |
| Phe | Lys | Asp | Phe | Gly 1735 | Asn | Met | Ser | Arg | Ala 1740 | Thr | Thr | Ser | Ile | Ala 1745 | |
| GCA | GGU | UAC | AAG | ACG | AUA | UCA | GAG | CUG | UGU | UCG | AAA | UUC | ACC | AAU | 5390 |
| Ala | Gly | Tyr | Lys | Thr 1750 | Ile | Ser | Glu | Leu | Cys 1755 | Ser | Lys | Phe | Thr | Asn 1760 | |
| UAC | UUG | GCU | GUA | ACC | UUC | UUU | GGG | GCG | CAA | GUU | GAU | GAC | GAU | GCU | 5435 |
| Tyr | Leu | Ala | Val | Thr 1765 | Phe | Phe | Gly | Ala | Gln 1770 | Val | Asp | Asp | Asp | Ala 1775 | |
| UUC | AAG | GGU | UUG | GUA | GCG | UUC | AAC | GUU | AAG | GAA | UGG | AUU | CUU | GAA | 5480 |
| Phe | Lys | Gly | Leu | Val 1780 | Ala | Phe | Asn | Val | Lys 1785 | Asp | Trp | Ile | Leu | Asp 1790 | |
| GUG | AAA | AAC | CUG | UCU | CUU | GAG | GAA | AAC | AAA | UUU | AGU | GGU | UUU | GGU | 5525 |
| Val | Lys | Asn | Leu | Ser 1795 | Leu | Glu | Asp | Asn | Lys 1800 | Phe | Ser | Gly | Phe | Gly 1805 | |
| GGU | GAU | GAG | CAU | CUU | GUC | AAG | GUU | AGA | CAU | UUA | UAU | GAU | AAA | UCU | 5570 |
| Gly | Asp | Glu | His | Leu 1810 | Val | Lys | Val | Arg | His 1815 | Leu | Tyr | Asp | Lys | Ser 1820 | |
| GUG | GAA | AUA | ACC | UAU | AAG | UUG | CUC | CAG | AAA | AAU | CGA | GUU | CCC | AUU | 5615 |
| Val | Asp | Ile | Thr | Tyr 1825 | Lys | Leu | Leu | Gln | Lys 1830 | Asn | Arg | Val | Pro | Ile 1835 | |
| GCU | AUG | CUU | CCU | AUC | AUC | CGA | GAC | ACG | UGU | AAG | AAG | UGC | GAG | GAU | 5660 |
| Ala | Met | Leu | Pro | Ile 1840 | Ile | Arg | Asp | Thr | Cys 1845 | Lys | Lys | Cys | Glu | Asp 1850 | |
| UUG | CUA | AAC | GAG | AGU | UAU | ACU | UAC | AAA | GGU | AUG | AAA | ACU | CCG | CGC | 5705 |
| Leu | Leu | Asn | Glu | Ser 1855 | Tyr | Thr | Tyr | Lys | Gly 1860 | Met | Lys | Thr | Pro | Arg 1865 | |
| GUG | GAC | CCA | UUC | UAU | AUA | UGC | CUU | UUU | GGA | GCA | CCU | GGA | GUU | GGC | 5750 |
| Val | Asp | Pro | Phe | Tyr 1870 | Ile | Cys | Leu | Phe | Gly 1875 | Ala | Pro | Gly | Val | Gly 1880 | |
| AAG | UCC | ACA | GUG | GCA | UCG | AUG | AUU | GUU | GAC | GAU | UUG | UUG | GAU | GCU | 5795 |
| Lys | Ser | Thr | Val | Ala 1885 | Ser | Met | Ile | Val | Asp 1890 | Asp | Leu | Leu | Asp | Ala 1895 | |
| AUG | GGC | GAA | CCU | AAG | GUU | GAU | AGG | AUC | UAU | ACG | CGA | UGC | UGU | UCU | 5840 |
| Met | Gly | Asp | Pro | Lys 1900 | Val | Asp | Arg | Ile | Tyr 1905 | Thr | Arg | Cys | Cys | Ser 1910 | |
| GAU | CAA | UAU | UGG | AGC | AAU | UAU | CAC | CAC | GAG | CCA | GUU | AUU | UGU | UAU | 5885 |
| Asp | Gln | Tyr | Trp | Ser 1915 | Asn | Tyr | His | His | Glu 1920 | Pro | Val | Ile | Cys | Tyr 1925 | |
| GAC | GAC | UUG | GGG | GCA | AUC | AGC | AGA | CCA | GCG | AGU | UUA | UCA | GAC | UAU | 5930 |
| Asp | Asp | Leu | Gly | Ala 1930 | Ile | Ser | Arg | Pro | Ala 1935 | Ser | Leu | Ser | Asp | Tyr 1940 | |
| GGG | GAG | AUA | AUG | GGA | AUC | AAA | UCG | AAC | AGA | CCA | UAC | UCC | CUA | CCU | 5975 |
| Gly | Glu | Ile | Met | Gly 1945 | Ile | Lys | Ser | Asn | Arg 1950 | Pro | Tyr | Ser | Leu | Pro 1955 | |
| AUG | GCU | GCU | GUU | GAU | GAG | AAA | GGA | AGG | CAU | UGU | UUA | UCG | CGA | UAC | 6020 |
| Met | Ala | Ala | Val | Asp 1960 | Glu | Lys | Gly | Arg | His 1965 | Cys | Leu | Ser | Arg | Tyr 1970 | |

| | |
|---|---|
| CUC AUU GCU UGU ACA AAU UUA ACC CAU CUG GAC GAU ACG GGC GAU<br>Leu Ile Ala Cys Thr Asn Leu Thr His Leu Asp Asp Thr Gly Asp<br>               1975                           1980                        1985 | 6065 |
| GUG AAA ACA AAG GAU GCC UAC UAU CGC AGA AUC AAU GUC CCA GUG<br>Val Lys Thr Lys Asp Ala Tyr Tyr Arg Arg Ile Asn Val Pro Val<br>               1990                           1995                        2000 | 6110 |
| ACA GUG ACG AGA GAA GUA ACC GCC AUG AUG AAC CCC GAG GAC CCA<br>Thr Val Thr Arg Asp Val Thr Ala Met Met Asn Pro Glu Asp Pro<br>               2005                           2010                        2015 | 6155 |
| ACU GAU GGA CUA CGU UUC ACC GUG GAG CAA GUG CUU GAU GGA GGU<br>Thr Asp Gly Leu Arg Phe Thr Val Glu Gln Val Leu Asp Gly Gly<br>               2020                           2025                        2030 | 6200 |
| AGA UGG AUU AAU GUU ACU GAA AGC CGU CUC CUC AAU GGA AGG AUG<br>Arg Trp Ile Asn Val Thr Asp Ser Arg Leu Leu Asn Gly Arg Met<br>               2035                           2040                        2045 | 6245 |
| CCA UUC AGG GCU GAA GAU CUC AUG AAC AUG AAC UAC AGU UAC UUU<br>Pro Phe Arg Ala Asp Asp Leu Met Asn Met Asn Tyr Ser Tyr Phe<br>               2050                           2055                        2060 | 6290 |
| AUG GAG UUU CUC AAG AUG UAU GCU GCU UUA UAU AUG GAA AAU CAA<br>Met Glu Phe Leu Lys Met Tyr Ala Ala Leu Tyr Met Asp Asn Gln<br>               2065                           2070                        2075 | 6335 |
| AAC AUG UUG GUG GCA AAA UUG AGA GGA ACA GAG AUC CCA GAA UCA<br>Asn Met Leu Val Ala Lys Leu Arg Gly Thr Glu Ile Pro Asp Ser<br>               2080                           2085                        2090 | 6380 |
| CGU AGU UCA GAG AAU GAA GAA CUU GAA UUC GAU UAU UUG GCU ACA<br>Arg Ser Ser Glu Asn Asp Asp Leu Asp Phe Asp Tyr Leu Ala Thr<br>               2095                           2100                        2105 | 6425 |
| GCU CAG AUG GAC CAU ACA GUG ACA UUU GGG GAA CUA GUU ACC AAA<br>Ala Gln Met Asp His Thr Val Thr Phe Gly Asp Leu Val Thr Lys<br>               2110                           2115                        2120 | 6470 |
| UUC AAC UCG UAU AAG CUU ACU GGG AAA CAA UGG AAC AAG AGG CUC<br>Phe Asn Ser Tyr Lys Leu Thr Gly Lys Gln Trp Asn Lys Arg Leu<br>               2125                           2130                        2135 | 6515 |
| UGG GAA CUU GGA UGG ACA UCU CUA GAC GGA UGG AAC ACG AAC AAG<br>Cys Asp Leu Gly Trp Thr Ser Leu Asp Gly Trp Asn Thr Asn Lys<br>               2140                           2145                        2150 | 6560 |
| AUU AUG AGA UUC GAC GAU CUA GUU GCC GGA UUC UGU GGU UGC UCA<br>Ile Met Arg Phe Asp Asp Leu Val Ala Gly Phe Cys Gly Cys Ser<br>               2155                           2160                        2165 | 6605 |
| AGG AAU GAG AAU UGC AAU UUU GAC UUC UAU CAU CAG AGA CUU CAA<br>Arg Asn Glu Asn Cys Asn Phe Asp Phe Tyr His Gln Arg Leu Gln<br>                                2170                        2175                        2180 | 6650 |
| GCA UGU UUG AAC AAG AAA GGG UUU GCU CCC GCA UAU CAA UAU UUC<br>Ala Cys Leu Asn Lys Lys Gly Phe Ala Pro Ala Tyr Gln Tyr Phe<br>                                2185                        2190                        2195 | 6695 |
| AAC CUU CAC AAG UUG AAU UCA GAC ACC CAG AAG ACA GAG CUC AAG<br>Asn Leu His Lys Leu Asn Ser Asp Thr Gln Lys Thr Glu Leu Lys<br>                                2200                        2205                        2210 | 6740 |
| CUU AAA UGC GGG ACA ACU GCU GAA GAU UUA UUC AGA CAA GCU GAC<br>Leu Lys Cys Gly Thr Thr Ala Glu Asp Leu Phe Arg Gln Ala Asp<br>                                2215                        2220                        2225 | 6785 |
| UUG AUG GUC AUA UUC UCC UAC CUC UUA UUU GUU GCG AGA AUU GGG<br>Leu Met Val Ile Phe Ser Tyr Leu Leu Phe Val Ala Arg Ile Gly<br>                                2230                        2235                        2240 | 6830 |
| GUG AGU GGA UCU CAU GUG UGU CUG UCA UAU AAC AUG UUG AAC GUC<br>Val Ser Gly Ser His Val Cys Leu Ser Tyr Asn Met Leu Asn Val<br>                                2245                        2250                        2255 | 6875 |
| AAG GAU GUC AAG GAU UUU GAG AUA UGC AGG GAG AAC GUU CUU GAU<br>Lys Asp Val Lys Asp Phe Glu Ile Cys Arg Glu Asn Val Leu Asp<br>                                2260                        2265                        2270 | 6920 |

| | | | | | | | | | | | | | | | |
|---|---|---|---|---|---|---|---|---|---|---|---|---|---|---|---|
| UUG | UCC | AGA | AAA | ACU | ACA | AUC | GAC | GGU | GAA | GAA | UGC | UAU | AUC | UGG | 6965 |
| Leu | Ser | Arg | Lys | Thr 2275 | Thr | Ile | Asp | Gly 2280 | Asp | Asp | Cys | Tyr | Ile 2285 | Trp | |
| AAU | UUU | AUU | UCU | GAU | AUC | UUC | CCA | CGC | AUU | GUG | GCU | AAG | UAC | AAC | 7010 |
| Asn | Phe | Ile | Ser | Asp 2290 | Ile | Phe | Pro | Arg 2295 | Ile | Val | Ala | Lys | Tyr 2300 | Asn | |
| UGU | GUU | GUG | CUU | AAC | GAC | GGA | GAG | AAG | AGA | UAC | AUC | UUC | GUG | ACU | 7055 |
| Cys | Val | Val | Leu | Asn 2305 | Asp | Gly | Glu | Lys 2310 | Arg | Tyr | Ile | Phe | Val 2315 | Thr | |
| GAC | AGC | GCG | CCC | ACU | AGG | AUC | UUU | CCC | GAU | UUG | GCU | UGG | UCA | GAU | 7100 |
| Asp | Ser | Ala | Pro | Thr 2320 | Arg | Ile | Phe | Pro 2325 | Asp | Leu | Ala | Trp | Ser 2330 | Asp | |
| CUU | AUU | UCC | GGC | AAG | CAA | GUU | GUG | AGU | CCA | AAC | AUU | AUC | AAA | GUG | 7145 |
| Leu | Ile | Ser | Gly | Lys 2335 | Gln | Val | Val | Ser 2340 | Pro | Asn | Ile | Ile | Lys 2345 | Val | |
| GCU | GGA | GAA | ACC | AAG | UCG | AAA | ACC | AUU | GCC | CCU | CUG | CUA | GCA | GAU | 7190 |
| Ala | Gly | Asp | Thr | Lys 2350 | Ser | Lys | Thr | Ile 2355 | Ala | Pro | Leu | Leu | Ala 2360 | Asp | |
| UCC | UAC | AAG | GUU | UUC | AAG | GAU | CCG | AAG | GCA | UGG | CUU | GAG | AGG | AAC | 7235 |
| Ser | Tyr | Lys | Val | Phe 2365 | Lys | Asp | Pro | Lys 2370 | Ala | Trp | Leu | Glu | Arg 2375 | Asn | |
| AAA | GAA | UUG | AAA | GCA | GCU | CUA | GAA | ACA | GAA | GAA | UAU | AUC | GCU | CUC | 7280 |
| Lys | Asp | Leu | Lys | Ala 2380 | Ala | Leu | Asp | Thr 2385 | Asp | Asp | Tyr | Ile | Ala 2390 | Leu | |
| CUC | UUU | GCU | GUU | GCA | UGU | GAA | GCU | GGU | AGA | UUC | ACU | CAA | AUU | UUA | 7325 |
| Leu | Phe | Ala | Val | Ala 2395 | Cys | Asp | Ala | Gly 2400 | Arg | Phe | Thr | Gln | Ile 2405 | Leu | |
| GAC | AAA | CCU | CCC | AGU | AGA | CGC | AAG | AUU | UUA | AAU | AUG | UCC | GAA | AGG | 7370 |
| Asp | Lys | Pro | Pro | Ser 2410 | Arg | Arg | Lys | Ile 2415 | Leu | Asn | Met | Ser | Asp 2420 | Arg | |
| UAU | AAU | GCA | UAU | AUU | GAA | CAG | GAA | AAA | GGG | CUG | AUU | GGG | AGA | CUU | 7415 |
| Tyr | Asn | Ala | Tyr | Ile 2425 | Asp | Gln | Asp | Lys 2430 | Gly | Leu | Ile | Gly | Arg 2435 | Leu | |
| UCU | AAA | CCA | GCA | AAG | AUA | UGC | UUA | GCC | AUA | GGA | ACU | GGA | GUU | GCG | 7460 |
| Ser | Lys | Pro | Ala | Lys 2440 | Ile | Cys | Leu | Ala 2445 | Ile | Gly | Thr | Gly | Val 2450 | Ala | |
| AUC | UUU | GGG | GCC | CUA | GCA | GGC | AUU | GGA | GUG | GGU | UUG | UUU | AAG | CUG | 7505 |
| Ile | Phe | Gly | Ala | Leu 2455 | Ala | Gly | Ile | Gly 2460 | Val | Gly | Leu | Phe | Lys 2465 | Leu | |
| AUA | GCU | CAC | UUC | AAC | AAA | GAU | GAA | GAA | GAG | GUA | GAC | GAA | AUU | GAA | 7550 |
| Ile | Ala | His | Phe | Asn 2470 | Lys | Asp | Asp | Asp 2475 | Glu | Val | Asp | Asp | Ile 2480 | Asp | |
| UUU | GAU | AUA | CUC | UCC | CCA | GAG | AUG | AGC | GGU | UCG | CAC | GAA | UCC | GGC | 7595 |
| Phe | Asp | Ile | Leu | Ser 2485 | Pro | Glu | Met | Ser 2490 | Gly | Ser | His | Asp | Ser 2495 | Gly | |
| CAA | CAU | ACC | ACG | AGG | UAC | GUC | ACG | AAG | GAG | CGA | GUU | CCA | UCC | AAA | 7640 |
| Gln | His | Thr | Thr | Arg 2500 | Tyr | Val | Thr | Lys 2505 | Glu | Arg | Val | Pro | Ser 2510 | Lys | |
| CCA | GCA | AGG | AGG | CAA | CAU | GAA | UUU | GAU | CUA | AUG | UUC | GAU | AAU | CUA | 7685 |
| Pro | Ala | Arg | Arg | Gln 2515 | His | Asp | Phe | Asp 2520 | Leu | Met | Phe | Asp | Asn 2525 | Leu | |
| CCC | ACU | CCA | CAA | GUU | GAA | GAG | CUA | AAG | AGU | GAG | AUG | ACC | UGC | GCC | 7730 |
| Pro | Thr | Pro | Gln | Val 2530 | Asp | Glu | Leu | Lys 2535 | Ser | Glu | Met | Thr | Cys 2540 | Ala | |
| AGU | GCC | AGU | GAU | GAG | CAU | AAG | ACU | CAG | UAU | GUU | AAA | AGA | AGA | GUG | 7775 |
| Ser | Ala | Ser | Asp | Glu 2545 | His | Lys | Thr | Gln 2550 | Tyr | Val | Lys | Arg | Arg 2555 | Val | |
| GGA | CCU | GUA | AGC | AAA | CGU | AAG | GAU | GCU | UCG | GUA | GCA | GAA | AUU | AGU | 7820 |
| Gly | Pro | Val | Ser | Lys 2560 | Arg | Lys | Asp | Ala 2565 | Ser | Val | Ala | Asp | Ile 2570 | Ser | |

```
GGA GCU CAU GCG AGU GAU CAG CAU CAU ACA GAA UAC UUG AAA GCA                    7865
Gly Ala His Ala Ser Asp Gln His His Thr Asp Tyr Leu Lys Ala
            2575            2580                2585

CGC GUU CCA CUC AUG AAA AGA AUA GCU ACC AAA GAG AGC UAU GUU                    7910
Arg Val Pro Leu Met Lys Arg Ile Ala Thr Lys Glu Ser Tyr Val
            2590            2595                2600

GUA ACU UAC GAU GAC GAA CCC AGC UCU CAU AUU UCC CUA GUU CGC                    7955
Val Thr Tyr Asp Asp Asp Pro Ser Ser His Ile Ser Leu Val Arg
            2605            2610                2615

AGG AUC CGA CGU ACA CGA CUG GCA AGA GCC AUC AAG CAA AUG GCA                    8000
Arg Ile Arg Arg Thr Arg Leu Ala Arg Ala Ile Lys Gln Met Ala
            2620            2625                2630

GUC CUG GAG GAC UUC CCA UCU ACC UUG GAA GAG AUA CGA CUU UGG                    8045
Val Leu Glu Asp Phe Pro Ser Thr Leu Asp Glu Ile Arg Leu Trp
            2635            2640                2645

AGA CAA AAC GCU GCA AAU AAA GGG GUU AUU GUU CCG AAG UAC UCA                    8090
Arg Gln Asn Ala Ala Asn Lys Gly Val Ile Val Pro Lys Tyr Ser
            2650            2655                2660

ACA AGU GGG AAA UUC UUC AGU GGC UUG UUG GAU GAU GAA GAA GAA                    8135
Thr Ser Gly Lys Phe Phe Ser Gly Leu Leu Asp Asp Glu Glu Asp
            2665            2670                2675

GAA CCU CAG AAU GUG AAU AUG UUG AAC GAA GAG GAC AUU GAG GUA                    8180
Asp Pro Gln Asn Val Asn Met Leu Asn Asp Glu Asp Ile Glu Val
            2680            2685                2690

GAU AAG CGA AUG UUU GAG AAG AUU UCU GAG GUU AUA AGC GUG AUU                    8225
Asp Lys Arg Met Phe Glu Lys Ile Ser Glu Val Ile Ser Val Ile
            2695            2700                2705

CAA CCC AGA AAG AAU GAG CUG GAA AGA AUG AUU GAG GAA GGC GUA                    8270
Gln Pro Arg Lys Asn Glu Leu Asp Arg Met Ile Glu Asp Gly Val
            2710            2715                2720

CAC CAC AAG GUC GUA AAG CAG GCA AGG GUU AAC GAC AAG GGC UUA                    8315
His His Lys Val Val Lys Gln Ala Arg Val Asn Asp Lys Gly Leu
            2725            2730                2735

GCC AAA GAC CCC AAC AUG GUG ACU AUC UUG ACG GAC AAA UUA AUU                    8360
Ala Lys Asp Pro Asn Met Val Thr Ile Leu Thr Asp Lys Leu Ile
            2740            2745                2750

AAU AUU AGU GCG GUG AUC GUC AAU UUA ACG CCG ACA CGC CGG GCA                    8405
Asn Ile Ser Ala Val Ile Val Asn Leu Thr Pro Thr Arg Arg Ala
            2755            2760                2765

UAC AUG AAC GUG GUA CGU CUU AUA GGC ACU AUA GUU GUU UGC CCA                    8450
Tyr Met Asn Val Val Arg Leu Ile Gly Thr Ile Val Val Cys Pro
            2770            2775                2780

GCC CAC UAC UUG GAA GCU UUA GAG GAA GGA GAU GAG CUG UAU UUC                    8495
Ala His Tyr Leu Asp Ala Leu Glu Glu Gly Asp Glu Leu Tyr Phe
            2785            2790                2795

AUU UGC UUC UCA UUG GUU AUC AAG CUC ACU UUU GAU CCA AGU AGA                    8540
Ile Cys Phe Ser Leu Val Ile Lys Leu Thr Phe Asp Pro Ser Arg
            2800            2805                2810

GUG ACU CUC GUG AAU AGC CAG CAG GAU UUG AUG GUU UGG GAU CUU                    8585
Val Thr Leu Val Asn Ser Gln Gln Asp Leu Met Val Trp Asp Leu
            2815            2820                2825

GGG AAC AUG GUA CCA CCC UCA AUU GAU ACU CUU AAA AUG AUA CCU                    8630
Gly Asn Met Val Pro Pro Ser Ile Asp Thr Leu Lys Met Ile Pro
            2830            2835                2840

ACG CUU GAA GAC UGG GAU CAC UUU CAG GAU GGA CCA GGA GCC UUU                    8675
Thr Leu Asp Asp Trp Asp His Phe Gln Asp Gly Pro Gly Ala Phe
            2845            2850                2855

GCU GUU ACG AAA UAU AAC UCG AAA UUC CCA ACC AAU UAU AUC AAC                    8720
Ala Val Thr Lys Tyr Asn Ser Lys Phe Pro Thr Asn Tyr Ile Asn
            2860            2865                2870
```

```
ACA CUG ACU AUG AUU GAG AGG AUU AGG GCA AAU ACU CAG AAU CCC         8765
Thr Leu Thr Met Ile Glu Arg Ile Arg Ala Asn Thr Gln Asn Pro
            2875            2880            2885

ACG GGU UGU UAU UCC AUG AUG GGC UCC CAA CAU ACA AUC ACC ACA         8810
Thr Gly Cys Tyr Ser Met Met Gly Ser Gln His Thr Ile Thr Thr
            2890            2895            2900

GGA UUG CGA UAU CAA AUG UUC UCU CUU GAU GGA UUC UGC GGU GGG         8855
Gly Leu Arg Tyr Gln Met Phe Ser Leu Asp Gly Phe Cys Gly Gly
            2905            2910            2915

UUA AUC CUG AGA GCC AGC ACA AAC AUG GUG AGA AAG GUC GUC GGG         8900
Leu Ile Leu Arg Ala Ser Thr Asn Met Val Arg Lys Val Val Gly
            2920            2925            2930

AUC CAC GUU GCU GGA AGC CAG AAU CAC GCU AUG GGA UAU GCA GAG         8945
Ile His Val Ala Gly Ser Gln Asn His Ala Met Gly Tyr Ala Glu
            2935            2940            2945

UGC CUU AUU GCA GAA GAU UUA CGG GCU GCA GUG GCG AGA UUG GCG         8990
Cys Leu Ile Ala Asp Asp Leu Arg Ala Ala Val Ala Arg Leu Ala
            2950            2955            2960

CUA GAU CCU AGA AGC ACC AUC CAG GCA AGU CUG AAA GGU AGG AUU         9035
Leu Asp Pro Arg Ser Thr Ile Gln Ala Ser Leu Lys Gly Arg Ile
            2965            2970            2975

GAU GCU GUU UCU AAA CAA UGU GGU UUA GAC AGA GCU CUG GGU ACG         9080
Asp Ala Val Ser Lys Gln Cys Gly Leu Asp Arg Ala Leu Gly Thr
            2980            2985            2990

AUA GGA UGU CAC GGG AAA GUU GCC UCU GAA GAU AUU ACA AGU GCC         9125
Ile Gly Cys His Gly Lys Val Ala Ser Asp Asp Ile Thr Ser Ala
            2995            3000            3005

GCC ACG AAA ACU UCC AUA AGA AAG UCA AGA AUA CAU GGU CUA GUG         9170
Ala Thr Lys Thr Ser Ile Arg Lys Ser Arg Ile His Gly Leu Val
            3010            3015            3020

GGU GAG AUU AGA ACU GAG CCU UCA AUU UUA CAC GCU CAU GAU CCC         9215
Gly Glu Ile Arg Thr Glu Pro Ser Ile Leu His Ala His Asp Pro
            3025            3030            3035

CGA CUG CCU AAA GAC AAG AUU GGG AAA UGG GAC CCG GUU AUU GAG         9260
Arg Leu Pro Lys Asp Lys Ile Gly Lys Trp Asp Pro Val Ile Glu
            3040            3045            3050

GCA UCA AUG AAG UAU GGU UCG AGA AUC ACA CCG UUC CCU GUA GAC         9305
Ala Ser Met Lys Tyr Gly Ser Arg Ile Thr Pro Phe Pro Val Asp
            3055            3060            3065

CAA AUU CUG GAA GUG GAG GAU CAU CUU UCU AAA AUG UUG GCC AAU         9350
Gln Ile Leu Glu Val Glu Asp His Leu Ser Lys Met Leu Ala Asn
            3070            3075            3080

UGU GAG AAU UCA AAA AAC AAG CGG CAG GUU AAU AAU CUA GAA AUA         9395
Cys Glu Asn Ser Lys Asn Lys Arg Gln Val Asn Asn Leu Asp Ile
            3085            3090            3095

GGG AUU AAU GGA AUU GAC CAG UCG GAU UAU UGG CAA CAG AUA GAA         9440
Gly Ile Asn Gly Ile Asp Gln Ser Asp Tyr Trp Gln Gln Ile Asp
            3100            3105            3110

AUG GAU ACU UCA AGU GGU UGG CCA UAC GCU AAG CGU AAA CCU GUU         9485
Met Asp Thr Ser Ser Gly Trp Pro Tyr Ala Lys Arg Lys Pro Val
            3115            3120            3125

GGG GCA GCU GGA AAG AAA UGG CUA UUC GAG CAA GAC GGC ACA UAU         9530
Gly Ala Ala Gly Lys Lys Trp Leu Phe Glu Gln Asp Gly Thr Tyr
            3130            3135            3140

CCC UCC GGA AAA CCU CGA UAU GUA UUU GGA GAU GCC GGG UUG AUU         9575
Pro Ser Gly Lys Pro Arg Tyr Val Phe Gly Asp Ala Gly Leu Ile
            3145            3150            3155

GAG AGC UAU AAC UCG AUG CUU GGU GAG GCG AAG CAA GGC AUU AGU         9620
Glu Ser Tyr Asn Ser Met Leu Gly Glu Ala Lys Gln Gly Ile Ser
            3160            3165            3170
```

| | | | | | | | | | | | | | | | |
|---|---|---|---|---|---|---|---|---|---|---|---|---|---|---|---|
| CCC | ACU | GUC | GUC | ACA | AUU | GAG | UGC | GCA | AAA | GAU | GAG | AGG | CGG | AAG | 9665 |
| Pro | Thr | Val | Val | Thr | Ile | Glu | Cys | Ala | Lys | Asp | Glu | Arg | Arg | Lys | |
| | | | 3175 | | | | 3180 | | | | | 3185 | | | |
| CUU | AAU | AAG | AUA | UAU | GAG | AAA | CCC | GCC | ACU | CGG | ACG | UUC | ACC | AUA | 9710 |
| Leu | Asn | Lys | Ile | Tyr | Glu | Lys | Pro | Ala | Thr | Arg | Thr | Phe | Thr | Ile | |
| | | | 3190 | | | | 3195 | | | | | 3200 | | | |
| CUG | CCA | CCU | GAG | AUU | AAU | AUU | UUA | UUC | AGG | CAG | UAU | UUC | GGA | GAU | 9755 |
| Leu | Pro | Pro | Glu | Ile | Asn | Ile | Leu | Phe | Arg | Gln | Tyr | Phe | Gly | Asp | |
| | | | 3205 | | | | 3210 | | | | | 3215 | | | |
| UUU | GCA | GCG | AUG | GUA | AUG | ACA | UGU | AGA | GCC | AAG | CUU | UUC | UGU | CAA | 9800 |
| Phe | Ala | Ala | Met | Val | Met | Thr | Cys | Arg | Ala | Lys | Leu | Phe | Cys | Gln | |
| | | | 3220 | | | | 3225 | | | | | 3230 | | | |
| GUU | GGC | AUC | AAC | CCA | GAG | UCA | AUG | GAG | UGG | GGU | GAU | CUC | AUG | CUA | 9845 |
| Val | Gly | Ile | Asn | Pro | Glu | Ser | Met | Glu | Trp | Gly | Asp | Leu | Met | Leu | |
| | | | 3235 | | | | 3240 | | | | | 3245 | | | |
| GGU | CUA | AAG | GAG | AAA | UCA | ACU | AAG | GGA | UUU | GCA | GGA | GAU | UAU | UCG | 9890 |
| Gly | Leu | Lys | Glu | Lys | Ser | Thr | Lys | Gly | Phe | Ala | Gly | Asp | Tyr | Ser | |
| | | | 3250 | | | | 3255 | | | | | 3260 | | | |
| AAG | UUC | GAU | GGA | AUC | GGA | GAC | CCC | CAG | AUU | UAU | CAU | UCA | AUU | ACC | 9935 |
| Lys | Phe | Asp | Gly | Ile | Gly | Asp | Pro | Gln | Ile | Tyr | His | Ser | Ile | Thr | |
| | | | 3265 | | | | 3270 | | | | | 3275 | | | |
| CAA | GUA | GUC | AAC | AAC | UGG | UAU | AAC | GAU | GGG | GAA | GAA | AAU | GCG | ACU | 9980 |
| Gln | Val | Val | Asn | Asn | Trp | Tyr | Asn | Asp | Gly | Glu | Glu | Asn | Ala | Thr | |
| | | | 3280 | | | | 3285 | | | | | 3290 | | | |
| AUC | AGG | CAU | GCU | CUG | AUA | AGU | AGC | AUU | AUA | CAC | AGG | CGG | GGC | AUU | 10025 |
| Ile | Arg | His | Ala | Leu | Ile | Ser | Ser | Ile | Ile | His | Arg | Arg | Gly | Ile | |
| | | | 3295 | | | | 3300 | | | | | 3305 | | | |
| GUG | AAA | GAA | UAU | UUG | UUC | CAG | UAU | UGC | CAG | GGU | AUG | CCA | UCA | GGG | 10070 |
| Val | Lys | Asp | Tyr | Leu | Phe | Gln | Tyr | Cys | Gln | Gly | Met | Pro | Ser | Gly | |
| | | | 3310 | | | | 3315 | | | | | 3320 | | | |
| UUC | GCC | AUG | ACA | GUG | AUA | UUC | AAU | UCG | UUU | AUG | AAC | UAU | UAU | UAU | 10115 |
| Phe | Ala | Met | Thr | Val | Ile | Phe | Asn | Ser | Phe | Met | Asn | Tyr | Tyr | Tyr | |
| | | | 3325 | | | | 3330 | | | | | 3335 | | | |
| CUG | UCU | UUG | GCC | UGG | AUG | AAU | CUG | AUA | AGU | GCA | UCC | CCC | CUU | AGU | 10160 |
| Leu | Ser | Leu | Ala | Trp | Met | Asn | Leu | Ile | Ser | Ala | Ser | Pro | Leu | Ser | |
| | | | 3340 | | | | 3345 | | | | | 3350 | | | |
| CCA | CAA | GCU | UCU | UUG | AGA | UAU | UUU | GAU | GAG | UAU | UGU | AAG | GUC | AUU | 10205 |
| Pro | Gln | Ala | Ser | Leu | Arg | Tyr | Phe | Asp | Glu | Tyr | Cys | Lys | Val | Ile | |
| | | | 3355 | | | | 3360 | | | | | 3365 | | | |
| GUU | UAC | GGU | GAU | GAU | AAU | AUU | GUU | GCC | GUC | AAC | GAA | GAA | UUC | UUA | 10250 |
| Val | Tyr | Gly | Asp | Asp | Asn | Ile | Val | Ala | Val | Asn | Asp | Asp | Phe | Leu | |
| | | | 3370 | | | | 3375 | | | | | 3380 | | | |
| GAG | UAC | UAU | AAC | UUG | AGG | CUU | GUG | GCA | GGC | UAU | CUU | AGU | CAA | UUU | 10295 |
| Glu | Tyr | Tyr | Asn | Leu | Arg | Leu | Val | Ala | Gly | Tyr | Leu | Ser | Gln | Phe | |
| | | | 3385 | | | | 3390 | | | | | 3395 | | | |
| GGA | GUA | AGC | UAC | ACU | GAU | GAC | GCC | AAG | AAC | CCA | AUA | GAG | AAG | AGC | 10340 |
| Gly | Val | Ser | Tyr | Thr | Asp | Asp | Ala | Lys | Asn | Pro | Ile | Glu | Lys | Ser | |
| | | | 3400 | | | | 3405 | | | | | 3410 | | | |
| GAA | CGA | UAU | GUG | AAG | AUA | GAA | GAC | GUU | ACG | UUC | UUA | AAA | CGG | CGA | 10385 |
| Asp | Arg | Tyr | Val | Lys | Ile | Asp | Asp | Val | Thr | Phe | Leu | Lys | Arg | Arg | |
| | | | 3415 | | | | 3420 | | | | | 3425 | | | |
| UGG | GUG | AGU | CUU | GGC | GGU | AGA | GCU | UCG | AUG | CUG | UAC | AAA | GCU | CCG | 10430 |
| Trp | Val | Ser | Leu | Gly | Gly | Arg | Ala | Ser | Met | Leu | Tyr | Lys | Ala | Pro | |
| | | | 3430 | | | | 3435 | | | | | 3440 | | | |
| CUU | GAC | AAG | GUU | AGC | AUU | GAG | GAA | AGG | CUU | AAC | UGG | AUC | AGA | GAG | 10475 |
| Leu | Asp | Lys | Val | Ser | Ile | Glu | Asp | Arg | Leu | Asn | Trp | Ile | Arg | Glu | |
| | | | 3445 | | | | 3450 | | | | | 3455 | | | |
| UGU | GAC | GAU | GGG | GAA | CUA | GCU | CUG | GUG | CAG | AAC | AUU | GAA | AGU | GCU | 10520 |
| Cys | Asp | Asp | Gly | Glu | Leu | Ala | Leu | Val | Gln | Asn | Ile | Asp | Ser | Ala | |
| | | | 3460 | | | | 3465 | | | | | 3470 | | | |

-continued

| | | | | | | | | | | | | | | |
|---|---|---|---|---|---|---|---|---|---|---|---|---|---|---|
| CUG | UAC | GAA | GCU | AGU | AUU | CAU | GGC | CAC | ACA | UAU | UUU | GGA | GAG | CUU | 10565 |
| Leu | Tyr | Asp | Ala | Ser | Ile | His | Gly | His | Thr | Tyr | Phe | Gly | Glu | Leu | |
| | | | 3475 | | | | 3480 | | | | | | | 3485 | |
| AAA | GAU | AAA | AUU | GCU | AAA | GCC | UGU | GAU | GCA | GUC | AUG | AUA | ACU | AUG | 10610 |
| Lys | Asp | Lys | Ile | Ala | Lys | Ala | Cys | Asp | Ala | Val | Met | Ile | Thr | Met | |
| | | | | 3490 | | | | 3495 | | | | | | 3500 | |
| CCA | AAU | AUA | AGA | UAU | AUU | GAC | UGC | CAG | AGA | CGA | UGG | UGG | ACC | UCC | 10655 |
| Pro | Asn | Ile | Arg | Tyr | Ile | Asp | Cys | Gln | Arg | Arg | Trp | Trp | Thr | Ser | |
| | | | | 3505 | | | | 3510 | | | | | | 3515 | |
| AUG | ACU | GGU | GGG | UAU | CUU | GAG | CCG | UCU | GAU | GUC | ACC | AAA | CUU | GUA | 10700 |
| Met | Thr | Gly | Gly | Tyr | Leu | Glu | Pro | Ser | Asp | Val | Thr | Lys | Leu | Val | |
| | | | | 3520 | | | | 3525 | | | | | | 3530 | |
| AGG | CUU | GUU | GAG | AAA | GGA | CUA | CUA | GAC | CCG | AAA | UCA | GUA | UGG | AAA | 10745 |
| Arg | Leu | Val | Glu | Lys | Gly | Leu | Leu | Asp | Pro | Lys | Ser | Val | Trp | Lys | |
| | | | | 3535 | | | | 3540 | | | | | | 3545 | |
| GAC | CCA | UUG | UAC | AGA | ACC | AAC | AAG | UUG | CUA | UUC | GAC | CUA | UUG | AGG | 10790 |
| Asp | Pro | Leu | Tyr | Arg | Thr | Asn | Lys | Leu | Leu | Phe | Asp | Leu | Leu | Arg | |
| | | | | 3550 | | | | 3555 | | | | | | 3560 | |
| GAG | GUU | AAG | GCA | GCA | CCC | CUG | GCC | GCA | UUU | GUG | GUC | UAA | | | 10829 |
| Glu | Val | Lys | Ala | Ala | Pro | Leu | Ala | Ala | Phe | Val | Val | | | | |
| | | | | 3565 | | | | 3570 | | | | | | | |

| | |
|---|---|
| GUUACCCUUC UGACAAAAGG GCCUUGAACG GUUAUGGUUG AACAGAACUG | 10879 |
| UAAAAGGUGA GGACUAUAUA AGUUGUAGUA CGGAUGAGAU UGAAAGAAAA | 10929 |
| UUGGGUCACU CCCAUUCCUU UAUUAGGAAG GAGUGAUACC UUUUGUGUAG | 10979 |
| AUCUCUACCC CGAAACUCUU GAACCCUCAC ACGUUUUGGA GUAACCAGUA | 11029 |
| CACCCUUUUA GGUGGACCCU CGACUAUAGA UCGAGACCAA GUAUUGACUU | 11079 |
| GGUGUUCACG UCUUGCCGGA CGCAAAAUGG CACCCUUGUU UAGUGAUAUC | 11129 |
| AAGGUUACAA AUGUCACGCC CCACUAGUAA AAGUUUUGGU AUAUACGCAU | 11179 |
| UCGAACCGCC AAUGUAUACG UGUUUUCCCU UUUACUUUUU GUAUGUCGUC | 11229 |
| GUGGUGACGA GAUGCACGCC UGGUCAGCGG GGAAUAAGUU CACUAUAUGA | 11279 |
| ACAGACUCCG GCGAGCGAGA CACGCUGUCG GCCUCGGGAG AGGGAACUAG | 11329 |
| CUCCAGGCAC UUAAAUCCUG AAGUGUUAGA ACUAAGCGUU UGAUCCUCCU | 11379 |
| CCGGGGGAAA GAGAACGCCA GUUCUUUAAG CCAUAACUCU AGUGAGUUGA | 11429 |
| AUCCUAUUCA UCCUUCUUAG GAUUAAGGAU UUCUGAAGUC UAUCAUGAAA | 11479 |
| AGUAGAUAGA AAGCAACACG UCAAUAACGU GGAACCUUUU CCGAGGAAGU | 11529 |
| AGGGUGCUUG UUCGAAAAUC AUGGUAGAUU CGGAAACAAU UUGCUUAGAG | 11579 |
| UGUGUCUUUU CGCGUUGGUA GUUCAACCGU UAGGGCUAGG CACACUUCUC | 11629 |
| CACGGGUUUG UGCUGCAGUA UUAAAUAUCA UUAAGGUACU GUGCUAUAGC | 11679 |
| GGAGAAAUUA CAAAGCGUUG AACACAUUGA CGAUGGGGCC CAAUGCGCAC | 11729 |
| CCGGAUGUGU UACGCACCGU UUUUCUCUGU GUCACUAUAG AUAAAAGUGG | 11779 |
| GGUAGC | 11785 |

( 2 ) INFORMATION FOR SEQ ID NO: 5:

( i ) SEQUENCE CHARACTERISTICS:
        ( A ) LENGTH: 45 bases
        ( B ) TYPE: nucleotide
        ( C ) STRANDEDNESS: single
        ( D ) TOPOLOGY: linear ( i i ) MOLECULE TYPE: viral RNA
        ( A ) DESCRIPTION: RNA codons for first 15 amino acids at
          5'end of MCDV coat protein 1 (CP1)

(iii) HYPOTHETICAL: No (xi) SEQUENCE DESCRIPTION: SEQ ID NO: 5:

```
GUU  UCA  UUG  GGU  CGG  UCA  UUU  GAG  AAU  GGA  GUG  CUU  AUU  GGU  AGU      45
Val  Ser  Leu  Gly  Arg  Ser  Phe  Glu  Asn  Gly  Val  Leu  Ile  Gly  Ser
               5                             10                         15
```

(2) INFORMATION FOR SEQ ID NO: 6:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide
    (A) DESCRIPTION: first 15 amino acids of MCDV coat protein 3

(iii) HYPOTHETICAL: No (xi) SEQUENCE DESCRIPTION: SEQ ID NO: 6:

```
Leu  Gln  Val  Ala  Ser  Leu  Thr  Asp  Ile  Gly  Asp  Leu  Ser  Ser  Val
               5                             10                         15
```

(2) INFORMATION FOR SEQ ID NO: 7:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide
    (A) DESCRIPTION: first 15 amino acids of MCDV coat protein 1

(iii) HYPOTHETICAL: No (xi) SEQUENCE DESCRIPTION: SEQ ID NO: 7:

```
Val  Ser  Leu  Gly  Arg  Ser  Phe  Glu  Asn  Gly  Val  Leu  Ile  Gly  Ser
               5                             10                         15
```